(12) United States Patent
Khazak et al.

(10) Patent No.: US 8,324,188 B2
(45) Date of Patent: Dec. 4, 2012

(54) COMBINATIONS OF ET-18-O-CH$_3$ AND ANTI-CANCER AGENTS FOR THE TREATMENT OF CANCER

(76) Inventors: Vladimir Khazak, Brooklyn, NY (US); Lutz Weber, Germering (DE)

(*) Notice: Subject to any disclaimer, the term of this patent is extended or adjusted under 35 U.S.C. 154(b) by 237 days.

(21) Appl. No.: 12/514,328

(22) PCT Filed: Nov. 9, 2007

(86) PCT No.: PCT/EP2007/062177
§ 371 (c)(1), (2), (4) Date: Dec. 29, 2009

(87) PCT Pub. No.: WO2008/055995
PCT Pub. Date: May 15, 2008

(65) Prior Publication Data
US 2010/0111930 A1  May 6, 2010

Related U.S. Application Data

(60) Provisional application No. 60/858,033, filed on Nov. 10, 2006.

(51) Int. Cl.
*A61K 31/66* (2006.01)
*A61K 31/685* (2006.01)
*A61K 31/33* (2006.01)
*A61K 31/513* (2006.01)
*A61K 31/535* (2006.01)

(52) U.S. Cl. .............. 514/76; 514/75; 514/77; 514/740; 514/49; 514/183; 514/261.1; 514/449

(58) Field of Classification Search .................. None
See application file for complete search history.

(56) References Cited

U.S. PATENT DOCUMENTS

| 5,149,527 | A | | 9/1992 | Weisenthal |
| 5,484,911 | A | * | 1/1996 | Hong et al. |
| 5,512,671 | A | * | 4/1996 | Piantadosi et al. |
| 6,514,519 | B1 | * | 2/2003 | Nagler |

OTHER PUBLICATIONS

Gajate et al., Intracellular triggering of Fas aggregation and recruitment of apoptotic molecules into Fas-enriched rafts in selective tumor cell apoptosis, J. Exp. Med. 200(3):353-365, Aug. 2, 2004.*

Cloughesy et al., Intra-artierial carboplatin chemotherapy for brain tumorsL A dose escalation study based on cerebral blood flow, J. Neuro-Oncology, 35:121-131, 1997.*

Berdel et al., Ether lipids in cancer chemotherapy, Keio J. Med. 39:75-78, 1990.*

Principe et al., Evaluation of combinations of antineoplastic ether phospholipids and chemotherapeutic drugs, Anti-Cancer Drugs, 3(6):577-587, 1992.*

Lucas et al., Targeting the P13K/Akt cell survival pathway to induce death of HIV-1 infected macrophages with alkylphospholipid compounds, PLoS One, 5(9):e13121, Sep. 2010.*

Dai, Q. et al., "Enhanced Sensitivity to the HER1/Epidermal Growth Factor Receptor Tyrosine Kinase Inhibitor Erlotinib Hydrochloride in Chemotherapy-Resistant Tumor Cell Lines," Clinical Cancer Research, vol. 11, pp. 1572-1578, 2005.

Gajate, C. et al., "Edelfosine and perifosine induce selective apoptosis in multiple myeloma by recruitment of death receptors and downstream signaling molecules into lipid rafts" Blood, vol. 109, pp. 711-719, 2006.

Hermann, T.W. et al., "The retinoid X receptor agonist bexarotene (Targretin) synergistically enhances the growth inhibitory activity of cytotoxic drugs in non-small cell lung cancer cells" Lung Cancer, vol. 50, pp. 9-18, 2005.

Na, Hye-Kyung et al., "Induction of cyclooxygenase-2 in Ras-transformed human mammary epithelial cells undergoing apoptosis." Annals of the New York Academy of Sciences Nov. 2002, vol. 973, pp. 153-160, 2002.

Noseda, A. et al., "In-Vitro Antiproliferative Activity of Combinations of Ether Lipid Analogues and DNA-Interactive Agents Against Human Tumor Cells" Cancer Research, vol. 48, pp. 1788-1791, 1988.

Van Schaeyboreck, S. et al., "Chemotherapy-induced epidermal growth factor receptor activation determines response to combined gefitinib/chemotherapy treatment in non-small cell lung cancer cells" Molecular Cancer Therapeutics, vol. 5, pp. 1154-1165, 2006.

International Search Report for corresponding PCT application No. PCT/EP2007/062177 dated Aug. 8, 2008.

* cited by examiner

*Primary Examiner* — Claire Kaufman
(74) *Attorney, Agent, or Firm* — K&L Gates LLP

(57) ABSTRACT

A method to determine the utility of small molecules as functional replacements (mimetics) for protein receptor ligands is described. The method uses cellular biological assays on a systematic array of compounds, comprising known protein receptor ligands and other biologically active molecules to determine if a proposed small molecule is a functional equivalent of a receptor ligand, having therapeutic utility as a pharmaceutically relevant and useful agent either alone or in combination with other molecules. Furthermore, the invention provides for a method for the treatment of cancer comprising administering a combination of ET-18-O-CH3 and an anti-cancer agent.

1 Claim, 3 Drawing Sheets

A 30 mg 1-O-octadecyl-2-O-methyl-glycero-3-phosphocholine

B 30 mg 1-O-octadecyl-2-O-methyl-glycero-3-phosphocholine + 5 Gy radiation

C

PBS + 5 Gy radiation

COMBINATIONS OF ET-18-O-CH₃ AND ANTI-CANCER AGENTS FOR THE TREATMENT OF CANCER

CROSS-REFERENCE TO RELATED APPLICATIONS

This application claims the benefit of International Patent Application No. PCT/EP2007/062177 filed on Nov. 9, 2007 and U.S. Provisional Patent Application No. 60/858,033 filed on Nov. 10, 2006, the disclosures of which are incorporated by reference herein.

FIELD OF THE INVENTION

This invention relates to methods for determining the utility of small molecules as mimetics of receptor ligands and to their therapeutic application

BACKGROUND OF THE INVENTION

Problems to find receptor ligand mimetics. Modulation of biological functions through agonistic or antagonistic receptor ligands typically aims at either blocking or moderating overtly active biochemical pathways or activating or restoring pathways that are believed to relate to or are causative to a certain disease.

Different to endogenous or xenobiotic proteins and antibodies that exhibit very often highly specific biological activities, small molecules are much less specific. Due to their limited size, small molecules bind to a number of different targets, which may lead to undesired side effects and makes their development as therapeutically useful agents a challenge. For example, careful preclinical and clinical studies are needed to establish a therapeutically useful dose window, to discover off-target effects and their implications in drug development. Particularly the discovery of selective small molecules that are functional mimetics of protein receptor ligands presents a challenge to drug discovery, as the interaction sites and their area between the receptor and its natural ligand are exceeding by far the interaction area provided by small molecules (P. Chene, *Chem. Med. Chem.* 2006, 1: 400-411). Prototype molecules that have been found in primary biological screens have often the potential to also interact with other receptors and being non-specific on a cellular level.

Moreover, while it has been possible to find small molecules that are antagonists of a given receptor/ligand interaction, it is considered more challenging to identify agonists. Therefore, there is a clear need for a method that may distinguish selective and functional small molecule receptor ligand mimetics from molecules that are "promiscuous" by binding to multiple targets in an undesired way.

Problems to find useful combination treatments. While significant advancements have been made in many diseases and especially in the therapy of tumors there is often still a limited benefit provided by single agents as monotherapies. This is not surprising, given that molecular pathways that are responsible for diseases are often redundant and variable between individual patients or between cell subclones within the same patient. It is therefore often unlikely that a treatment focusing on a single target would offer durable disease control or therapy in most patients (J. E. Dancey and H. X. Chen, *Nat. Rev. Drug Discov.* 2006, 5:649-659). The use of drug combinations offers a well-established therapy principle, especially in cancer therapy, to provide a better therapy and benefit to patients. With few exceptions, useful drug treatments for cancer use a combination of agents of known activity and minimally overlapping spectra of toxicity, at their optimal doses and according to schedules that are compatible with normal cell recovery. Only few of those chemotherapeutic combinations have been critically evaluated pre-clinically and still fewer of these combinations are synergistic—providing greater benefit in their combination than by the additive effects of their individual activities. Many current combination treatments have been first tried in clinical studies—using a trial-and-error approach with human patients.

This largely empirical approach in clinical development towards combination therapies has been justified by the lack of means of identifying, which tumors might be sensitive to a combination of individual agents: There is a considerable lack of correlation between the outcomes of laboratory in vitro and in vivo experiments and clinical human studies because of the inherent limitations of in vitro and in vivo disease models. In addition, permanent cancer cell lines as for example provided by organizations like the ATCC or used by the National Cancer Institute show considerable alterations in biological properties and chemosensitivity patterns when compared with the original tumors from which they derive. Two studies have shown the limited correlation between in vitro testing in the 60-cell-line panel in the National Cancer Institute, in vivo xenografts and clinical efficacy of cytotoxic agents (J. I. Johnson, *Br. J. Cancer* 2001, 84: 1424-1431; T. Voskoglou-Nomikos et al., *Clin. Cancer Res.* 2003, 9: 4227-4239).

Second, methods are also needed to provide information on optimal treatment sequences of the combination. For example, laboratory studies have revealed that the EGFR inhibitor gefitinib is more effective in vitro in combination with standard cytotoxic agents given as a highdose 'pulse' prior to paclitaxel when compared with continuous, concurrent administration (D. B. Solit, *Clin. Cancer Res.* 2005, 11: 1983-1989).

Therefore, methods to rationally design and to experimentally validate synergistic drug combinations are urgently needed as they are expected to provide larger and durable therapeutic benefit for cancer patients.

Apoptosis is mediated through membrane bound receptors. Programmed cell death, termed apoptosis mediates the maintenance of tissue homeostasis, regulating removal of cells from the skin and gastrointestinal tract and remodeling of bone in response to environmental triggers. Apoptosis also prevents diseases by inhibiting systemic viral infection, deleting self-reactive T cells and B cells to prevent autoimmunity, and ablating cells that acquire potentially oncogenic characteristics. Dysregulation of apoptosis plays a role in many disease processes. Inappropriate activation of apoptosis is associated with neurodegenerative disorders such as Parkinson's and Alzheimer's disease, or myocardial damage seen after reperfusion of cardiac tissue following an infarct. Furthermore, if foreign epitopes are detected on the cell surface, apoptosis can be selectively induced by natural killer (NK) cells or cytotoxic T lymphocytes (CTL) of the immune system. Resistance to apoptosis or a higher threshold at which cells undergo apoptosis is associated with mutations in many genes, such as the p53 tumor suppressor gene. Hyperproliferating cells, which have defects in apoptotic pathways, may demonstrate a survival advantage, leading to further malignant progression and ultimately cancer.

The intrinsic (or mitochondrial) and the extrinsic apoptosis (or receptor mediated) pathway are two mechanisms through which apoptosis can occur.

In the intrinsic pathway, the functional consequence of proapoptotic signaling is the perturbation of the mitochondrial membrane and the release of cytochrome c into the cytoplasm. Here, cytochrome c forms a complex with apoptotic protease activating factor 1 (APAF1) and the inactive form of caspase-9, termed the apoptosome. This complex hydrolyzes adenosine triphosphate to cleave and activate caspase-9. This initiator caspase proceeds to cleave and activate the executioner molecules, caspase-3, caspase-6, and caspase-7. Release of cytochrome c from mitochondria is an early event of apoptosis that precedes caspase and endonuclease activation. The release of cytochrome c also leads to the formation of reactive oxygen species (ROS).

Apoptosis induced by the extrinsic apoptotic pathway is mediated through the activation of cell surface death receptors. After ligand mediated activation of a death receptor, the conserved intracellular death domain attracts the intracellular adapter molecule, Fas-associated death domain (FADD). The adapter molecule recruits caspase-8 and caspase-10 to the death receptor, forming the death-inducing signal complex (DISC), where they are cleaved and activated. In some cells, these initiator caspases are sufficient to cleave and activate the terminal executioner molecules, caspase-3, caspase-6, and caspase-7. However, some cells also require activation of the mitochondria-based apoptosis system to amplify the death receptor signal. Caspase-8 and caspase-10 cleave and activate the cytoplasmic proapoptotic factor Bcl-2 interacting domain (BID), which translocates to the mitochondria and induces release of the apoptosis initiating factor cytochrome c (E. K. Rowinsky, *Clin. Oncol.* 2005, 23: 9394-9407). A number of different receptors of the death receptor family as well as their natural ligands are known (Table 1.):

TABLE 1

Death receptors and their ligands

| Receptor | Ligand |
|---|---|
| TNFR1 (DR1) | TNF-α, LT-α |
| FAS (CD95, APO-1, DR2) | FasL |
| TRAIL-R1 (DR4) | TRAIL |
| TRAIL-R2 (DR5) | TRAIL |
| DR3 (APO2) | TL1, VEGI |
| DR6 | ? |
| NGFR | NGF |
| EDAR | Eda |

While many cytotoxic agents like cis-platinum or doxorubicin as well as radiation therapy appear to activate the intrinsic apoptosis pathway, targeted induction of apoptosis via the extrinsic apoptotic pathway represents an unexploited but emerging therapeutic strategy to destroy cancer cells. The activation of cell surface receptors by the tumor necrosis factor-related apoptosis-inducing ligand (TRAIL) results in direct stimulation of apoptotic signaling pathways (extrinsic stimulation). Molecules that directly activate these receptors, such as agonistic monoclonal antibodies to the TRAIL or Fas receptor (such as CH-11) and recombinant TRAIL or Fas Ligand (FasL), are being evaluated as potential monotherapies and as part of combination therapies with existing chemotherapeutic drugs and other therapeutic modalities.

TRAIL, TNFβ, FasL, and other TNF superfamily ligands demonstrated the ability to both initiate apoptosis and kill transformed cells, virally infected cells, and chronically activated T cells and B cells (S. R. Wiley et al., *Immunity* 1995, 3: 673-682; P. T. Daniel and P. H. Krammer, *J. Immunol.* 1994, 152: 5624-5632).

However, systemic therapeutic administration of recombinant TNFα (and similarly TRAIL in animal studies) in cancer patients results in a massive inflammatory response, as well as direct hepatotoxicity (A. L. Jones and P. Selby, *Cancer. Surv.* 1989, 8: 817-836).

One version of recombinant TRAIL, Apo2L/TRAIL (PRO1762), is currently being studied in phase I clinical trials. (A. Almasan and A. Ashkenazi, *Cytokine Growth Factor Rev.* 2003, 14: 337-348).

HGS-ETR1 (mapatumumab; Human Genome Sciences), a fully human agonistic monoclonal antibody that targets TRAIL-R1, is in phase II evaluations in patients with advanced malignancies. Fully human monoclonal antibodies to TRAIL-R2 (HGS-ETR2; Human Genome Sciences), such as HGS-TR2J, have also entered the clinic and are currently in phase I clinical development. HGS-ETR2 and HGS-TR2J have slightly different physiochemical and kinetic profiles that warrant the exploration of both in the clinic (R. Humphreys, et al., *Ann. Oncol.* 2004, 15: iii102, abstr. 383PD; R. Humphrey, et al., *Presented at the* 16th EORTC-NCI-AACR Symposium on Molecular Targets and Cancer Therapeutics, Geneva, Switzerland, Sep. 28-Oct. 1, 2004, abstr 204).

Especially promising appear therapeutic strategies where agents are combined that activate both the extrinsic and intrinsic pathway. Thus, ETR1 or ETR2 display synergies with cis-platin, camptothecin, topotecan, doxorubicin, gemicitabine, FU, vincristine, or paclitaxel in vitro, showing even activity in cell lines that do not go into apoptosis by treatment with either of the single agents (E. K. Rowinsky, *Clin. Oncol.* 2005, 23: 9394-9407).

Therefore, it appears highly desirable to find small molecules that are agonists of the FAS receptor and this receptor and its agonistic anti-body CH-11 shall provide an example for validating the method to find small molecule receptor ligand mimetics according to the present invention.

Multi-drug resistance (MDR). MDR is a major obstacle to the effective treatment of cancer. Drug resistant cancers are either inherently untreatable (intrinsic resistance) or they have progressed to develop resistance to a wide variety of anticancer agents over the course of treatment (acquired resistance). The term MDR is used to describe the ability of tumor cells exposed to a single cytotoxic agent to develop resistance to a broad range of structurally and functionally unrelated drugs. Numerous mechanisms are known to contribute to this phenomenon, including overexpression of drug efflux pumps, increased activity of DNA repair mechanisms, altered drug target enzymes, and overexpression of enzymes involved in drug detoxification and elimination. Because most chemotherapy approaches ultimately elicit their effects via apoptosis, alterations at the level of apoptosis control provide yet another mechanism by which drug resistance may occur. This review will focus on some of the strategies that have been used in an attempt to chemosensitize resistant tumors by manipulating dysregulated apoptosis pathways.

Mechanisms of drug resistance may be mediated by alterations in apoptosis pathways: the decision as to whether a cell undergoes apoptosis or continues to progress through the cell cycle is dependent on the interplay of a complex set of genes and proteins that interact to regulate cell cycle progression. Drug resistance can emerge if cells alter the expression of proteins that regulate the propagation of signals arising from cellular insults, such as chemotherapy, to protect against apoptosis. Although many details of the apoptotic pathway are still not completely understood, several proteins are known to be important regulators of this process.

A small molecule prototype. To validate the method to find small molecule receptor ligand mimetics according to the present invention and to demonstrate its utility, we further selected a small molecule well established in the art. This molecule is referred to herein as "AP-121" (alternative designations are edelfosine, ET-18-OCH3, 1-O-octadecyl-2-O-methyl-glycero-3-phosphocholine, rac-1-O-octaclecyl-2-O-methyl-glycero-3-phosphocholine or some times alkyllysopholid or ALP). AP-121 is an etherlipid, more precisely an alkyl-lysophospholipid, having the following chemical formula:

AP-121 is a synthetic analog of platelet activating factor (PAF; 1-O-alkyl-2-acetyl-sn-glycero-3-phosphocholine), which is generally believed to be involved in a variety of physiological processes, such as inflammation, the immune response, allergic reactions, reproduction and also have been shown to be effective as anti-tumor agent in mammals.

Cancer chemotherapy generally aims to slow the growth of, or destroy, cancer cells while avoiding collateral damage to surrounding cells and tissues. Consequently, the most effective anticancer agents are those that are able to selectively target cancer cells while leaving normal cells relatively unaffected.

Etherlipids are known to be effective anticancer agents in vitro and in animal models. Several mechanisms of action have been proposed for the toxicity of etherlipids towards cancer cells, including the cells' lack of alkyl cleavage enzymes. The resultant inability to metabolize the etherlipids leads to their intracellular accumulation and to consequent damage to cell membrane lipid organization. Other potential mechanisms of etherlipid action include effects on levels of intracellular protein phosphorylation, and disruption of cellular lipid metabolism. Normal cells typically possess the means to avoid or overcome the potentially toxic effects of etherlipids, while cancer cells do not.

AP-121 appears to exhibit multiple biological activities, including inhibition of the PI3K-Akt/PKB survival pathway, interaction with protein kinase C, intracellular activation of the Fas/CD95 death receptor, intracellular acidification, promotion of cytokine production, and altered plasma membrane function and lipid synthesis (G. Arthur and R. Bittman, *Biochim. Biophys. Acta* 1998, 1390: 85-102; ID, Berkovic, *Gen. Pharmacol.* 1998, 31: 511-517).

A liposomal formulation of AP-121, ELL-12 was found to be more effective than free AP-121 against leukemia, lung cancer metastases, and melanoma at lower and nontoxic dosing schedules (I. Ahmad et al., *Cancer Res.* 1997, 57: 1915-1921).

In a further example, AP-121 has been administered per orally dissolved in milk to patients with advanced non-small cell lung cancer in a phase II trial (P. Drings et al., *Onkologie* 1992, 15:

In particular, the in vitro and some of the animal data is suggesting a very broad "unspecific" activity in a range of tumors—which clearly could not be proven in the published human trials. In addition, some of the biological data obtained is also contradictory which may be attributed to the different assay systems, such as different cell lines that have been used, or the different experimental conditions or the skills of the involved scientists.

For example, AP-121 has been described and is sold as an experimental molecule that is an activator of membrane bound protein kinase C (PKC) in HL-60 cells at a concentration of 20 μg/ml (E. C. Heesbeen et al., *FEBS Lett.* 1991, 290:

231-4). AP-121 has been found to be competitive with phosphatidylserine binding to the regulatory domain of PKC. AP-121 was also described as an inhibitor of PKC (L. W. Daniel et al., *Cancer Res.* 1995, 55: 4844-9). By others it was found that PKC is inhibited at medium AP-121 concentrations, but activated at low and high concentrations (J. D. Aroca et al., *Eur. J. Biochem.* 2001, 268: 6369-78). Others describe that PKC is not involved in the cytotoxic action of AP-121 in HL-60 and K562 cells (E. C. Heesbeen et al., *Biochem. Pharmacol.* 1994, 47: 1481-8). AP-121 progressively inhibited the activity of PKC alpha as the concentration was increased up to 30 mol % of the total, lipid, above which the effect was one of activation. On PKC epsilon AP-121 had a triphasic effect, activating the enzyme at low concentrations, inhibiting it at slightly higher concentrations and then activating it again at higher concentrations (P. Conesa-Zamora et al., *Biochim. Biophys. Acta* 2005, 1687: 110-9).

AP-121 has been also described to inhibit the association between Ras and Raf-1, a know protein interaction that promotes tumor growth (P. Samadder et al., *Anticancer Research* 2003, 23: 2291-5). Sub-micromolar doses of AP-121 induced rapid internalization, but not activation, of epidermal growth factor receptor (EGFR), a known anti-cancer target, and concomitant MAPK/ERK activation in A431 cells (G. A. Ruiter et al., int. *J. Cancer* 2002, 102: 343-50). AP-121 reduced the number of receptor sites without affecting the affinity of EGF receptors in breast cancer MCF-7 and ZR-75-1 cell lines. When added at micromolar concentrations (5-25 μM), AP-121 inhibits growth factor-induced MAPK/ERK activation, at nM doses (10-500 nM). The activation of the MAPK/ERK pathway by AP-121 in A431 cells without stimulating cell proliferation: strikingly, AP-121 (500 nM) also triggered rapid clustering and internalization, of the EGFR in A431 cells (H. Kosano and O. Takatani, *Cancer Research* 1988, 48: 6033-6).

AP-121 has been also described to inhibit the phosphorylation and activation of p70 S6 kinase in MCF-7 cells (G. Arthur et al., *Anticancer Research* 2005, 25: 95-100). Inhibition of Na,K-ATPase and sodium pump by AP-121 was described by others (K. Oishi of al., *Biochem. Biophys. Res. Commun.* 1988, 157: 1000-6). Activation c-Jun NH2-terminal kinase and subsequent stimulation of apoptosis by A-121 was described (C. Gajate et al., *Mol. Pharmacol.* 1998, 53: 602-12).

Inhibition of PI3K-AKT/PKB pathway by AP-121 seems important, as increased activity of Akt and PI3K and mutations in PTEN, its negative regulator, are associated with malignancy and render cells insensitive to apoptosis induction (M. I. Berggren, et al., *Cancer Research* 1993, 53: 4297-302). Thus, AP-121 may inhibit functional PI3K activation by insulin. Downstream of AKT, AKT deactivates SEK-1, which is an activator of SAPK/JNK cascade. Thus, deactivating AKT with AP-121 allows activating the pro-apoptotic SAPK/JNK proteins (see Table 2, G. A. Ruiter, et al., *Anticancer Drugs* 2003, 14: 167-73).

TABLE 2

ED50 values (μM) for induction of apoptosis by ALP's AP-121, HePC and perifosine in the human epithelial carcinoma cell lines A431 and HeLa (mean ± SD from three independent experiments.

|  | AP-121 | HePC | Perifosine |
|---|---|---|---|
| A431 | 15.47 ± 2.9 | 17.27 ± 3.0 | 23.17 ± 2.7 |
| HeLa | 5.17 ± 1.6 | 8.17 ± 0.4 | 9.27 ± 1.8 |

Phospholipase C inhibition by AP-121 was described, leading to a Muscarinic receptor 1 and opiod receptor δ block, with a potential application of AP-121 in antinociception. (L. F. Horowitz et at, *J. Gen. Physiol* 2005, 126: 243-62).

Apoptosis triggered by AP-121 is prevented by increased expression of Phosphocholine Cytidyltransferase (CTP) (I. Baburina and S. Jackowski, *J. Biol. Chem.* 1998, 279: 2169-2173), suggesting CTP as a primary target of AP-121.

A connection was made to the inhibition of sphingosine-1-phosphate (S1P) S1P1 receptor mediating suppression of T cell migration (G. Dorsam et al., *J. Immunol.* 2003, 171: 3500-7). S1P prevents the hallmarks of apoptosis resulting from elevated levels of ceramide induced by TNFα, anti-Fas antibody, sphingomyelinase, or cell-permeable ceramide. Up-regulation of the sphingosine kinase enzyme responsible for its production may contribute to MDR by protecting the cell from apoptosis (O. Cuvillier et al., *Nature* 1996, 381: 800-3). Jurkat cells treated with anti-Fas monoclonal antibody (clone CH-11) underwent extensive cell death within 3 h. Fas ligation induces SAPK/JNK activation in Jurkat T cells. Fas ligation induces PARP cleavage, through a significant increase in caspase-3, caspase-6 and caspase-7 proteolytic PARP activity—S1P markedly decreased caspase-3, caspase-6 and caspase-7 activity (O. Cuvillier et al., *J. Biol. Chem.*, 1998, 273: 2910-16).

Gajate published on the ability of AP-121 to induce clustering of the FAS receptor in lipid rafts reasoning that this results in the ability of AP-121 to induce apoptosis (C. Gajate et al., *J. Exp. Med.* 2004, 200: 353-365). This putative AP-121 target was also shown in lymphoma cells and cell lines (C. Gajate and F. Mollinedo, *Blood* 2001, 98: 3860-3863). On the other hand, Spiegel and coworkers attribute these pro-apoptotic properties to the release of cytochrome c from mitochondria (O. Cuvillier et al., *Blood* 1999, 94: 3583-3582), independent of the FAS receptor. AP-121 is internalized into lipid rafts of tumor cells via endocytosis (A. H. van der Luit et al., *J. Biol. Chem.* 2002, 277: 39541; A. H. van der Luit, et al., *J. Biochem.* 2003, 374: 747). Once in the cell, AP-121 triggers recruitment of Fas-associated death domain protein, procaspase-8 and procaspase-10, c-Jun N-terminal kinase, and Bid, the molecules critical for initiation of apoptosis (C. Gajate et al., *Exp. Med.* 2004, 200: 353). Thus, death receptor (FAS-R) and mitochondrial apoptotic routes are spaciously linked, resulting in disruption of the mitochondrial transmembrane potential, production of reactive oxygen species, caspase-3 activation, cleavage of poly(ADP-ribose) polymerase, and DNA fragmentation (C. Gajate et al., *Int. J. Cancer* 2000, 86, 208.).

Compared to the reported biological activities of AP-121 in cell lines which is in the low micromolar range, the most potent effect described to date to our present knowledge is the anti-angiogenic activity of 60 nanomolar on HMEC1 endothelial cells (D. Candal, *Cancer Chemother. Pharmacol.* 1994, 34: 175-178).

Based on these biological data on various cells and cell lines, it appears that a method is needed to discover a biologically effect of AP-121, if there is any, that is of therapeutic relevance for a specific therapeutic indication.

Despite the uncertainty of its biological effect, U.S. Pat. No. 5,149,527 describes immunopotentiating compositions comprising etherlipids as suitable agents giving rise to tumor necrosis and/or regression in subjects who have previously received successful therapy, which destroys tumors and stimulates cytotoxic macrophages. The agents should be administered at a time when formation of macrophages specifically cytotoxic for the tumor have been generated by previous therapy. However, no data has been provided to support this activity of AP-121.

AP-121 has been described as a compound useful to treat cancer (DE 02 619 686) by administering to the mammals a pharmaceutically effective amount of AP-121 to reduce the size of tumors has been also described in U.S. Pat. No. 6,514, 519 and EP 1 079 838, being especially suitable for the treatment of primary and secondary malignant brain tumors.

U.S. Pat. No. 6,235,729 is directed to a method of inhibiting tumor progression in slowing or inhibiting tumor invasiveness and metastasis, comprising the step of administering to said individual a pharmacologically effective dose of a phospholipase C inhibitor, such as AP-121. Preferably, the phospholipase C inhibitor decreases phospholipase Cy. Generally, such a phospholipase C inhibitor would be administered in a dose of from about 0.1 mg/kg to about 2 mg/kg. While there is no data provided to support the claim, the dose reported will not reflect the low activity of AP-121, found in in vitro tests elsewhere.

AP-121 has been also reported to be useful to treat multiple sclerosis (MS; EP 2 363 901, DE 03 530 767) or rheumatoid arthritis (RA) or ankylosing spondylitis (AS; EP 474 712), by inhibition of activated CD4+ or CD8+ cytotoxic T-lymphocytes (CTL).

SUMMARY OF THE INVENTION

The present invention comprises a method to determine if a small molecule is a therapeutically useful receptor ligand functional mimetic. The present invention also refers to therapeutically useful treatment and diagnostic methods and compositions containing AP-121 either alone or in combination with other therapeutically useful compounds and methods to establish their therapeutic utility.

According to the present invention, the biological effect of a functional receptor ligand such as an endogenous or artificially made protein, peptide or antibody is measured against a panel of at least two different primary human cells or permanent cell lines alone and in combination with a panel of other compounds giving rise to an array of biological results. In parallel, the putative small molecule ligand mimetic is also measured against the same panel of at least two different primary human cells or permanent cell lines alone and in combination with the same panel of other compounds to give a second array of biological results. If the similarity, as calculated by a customary mathematical algorithm, of these two arrays is higher than a predefined threshold, the small molecule may be considered as a true receptor ligand mimetic, to be used as a therapeutic agent. In addition, the method according to this invention also delivers therapeutically useful combinations of small molecules that may act synergistically in diseases where the modulation of said receptor provides a therapeutic effect.

DETAILED DESCRIPTION OF THE INVENTION

The present invention refers to a novel method to determine if a small molecule is a functional and therapeutically useful mimetic of a receptor ligand.

A "small molecule", as used herein, comprises inter alia peptides, proteins, nucleic acid molecules, carbohydrates, lipids as well as low molecular weight chemical compounds.

Peptides and proteins that can be used in the present invention comprise naturally occurring as well as artificially designed molecules, for example by means of recombinant DNA technology or via chemical synthesis. They have a length of typically at last 800 amino acids, preferably of at last 600 amino acids, more preferably of at last 400 amino acids, and most preferably at last 200 amino acids.

Examples of nucleic acids that can be used in the present invention include naturally occurring nucleic acids such as deoxyribonucleic acid (DNA) or ribonucleic acid (RNA) as well as nucleic acid analogs. Such nucleic acids can be of any length and can be either single-stranded or double-stranded molecules.

Examples of carbohydrates that can be used in the present invention include monosaccharides such as glucose or fructose, disaccharides such as lactose or sucrose, as well as oligosaccharides and polysaccharides such as starch, with monosaccharides being preferred.

Examples of lipids that can be used in the invention include fatty acids, triacyl glycerides, sphingolipids, and phosphlipids. In preferred embodiments of the invention, the small molecules are selected from ether lipid, preferably alkyllysophopholipids, with AP-121 being particularly preferred.

The term "low molecular weight chemical compound", as used herein, denotes a molecule, preferably an organic molecule, comprising at least two carbon atoms, but preferably not more than seven carbon bonds, having a molecular weight in the range between 100 and 2.000 Dalton, preferably between 100 and 1.000 Dalton, and optionally including one or two metal atoms. Examples of such molecules include inter alia imidazoles, indoles, isoxazoles, oxazoles, pyridines, pyrimidines, and thiazoles As a first step of the method according to this invention, a therapeutically relevant receptor target has to be selected, as well as a suitable ligand that exerts a modulating effect, wherein the term "modulating effect", as used herein, comprises both an antagonistic (i.e. blocking or inhibiting) and an agonitic (i.e. activating) effect on the downstream signaling of the selected receptor. This selected ligand can be the endogenous ligand of the selected receptor or any other protein or peptide, such as an anti-body, that is known to exhibit this effect. This ligand does not need to exhibit properties that are useful for drug like molecules, rather it is important that the ligand exhibits its effect selectively and is devoid of properties that make its use as a tool for cell based screening difficult or impossible. Further, a small molecule has to be selected that is a putative receptor ligand mimetic, together with a panel of at least one, preferably at least two, and more preferably at least three other molecules that are know to exhibit a biological effect.

In a second step of the present method, a panel of at least two but more preferred at least three primary cells of different human origin and/or permanent, human derived cell lines have to be selected. These cell lines preferentially will express the selected receptor in different levels, and/or with a different mutational status and/or different concentration in the cellular membrane, ensuring that a correlation of the biological effect with such receptor levels can be derived from the measured biological effect.

In a third step, the biological effects of the selected various compounds are measured. According to the present invention, under the term "biological effect" a variety of cell-based, biological assays to measure such effect can be used. For example, but not limited to, gene expression such as RT-PCR, protein level detection, or more complex biological events such as inhibition of proliferation, colony formation, angiogenesis or apoptosis can be measured.

The "biological effect" according to the present invention may be also a summary or averaged result of several biological assays, either through repeated experimentation, using different concentrations or involving assays of different nature. Thus, a biological effect can be an 50% inhibitory concentration (IC50), effective dose (ED50), combination index (CI) or alike. According to the present method, the compounds are now measured in the following way to obtain two arrays of biological results: first, the biological effects of the receptor ligand on each individual cell line (from 1 to N, where N is the number of different cells) is measured, preferentially by repeating the same experiment multiple times to obtain reliable results. Next, the receptor ligand is combined in predefined ratios with each of the other compounds individually to obtain two-compound mixtures.

These two-compound mixtures may also contain mixtures of the same ligand and compound, but in different ratios (1 to M, where M is the number of different compound mixtures). Following this, the biological effects of each mixture on each individual cell line (from 1 to N, where N is the number of different cells) is measured, preferentially by repeating the same experiment multiple times to obtain reliable results. As a result we obtain a two-dimensional array (A1) of biological results.

In a fourth step, the third step is repeated by replacing the receptor ligand with the putative small molecule which is also measured in the same way against the same panel of at least two different primary cells or permanent cell lines alone and in combination with the same panel of other compounds to give a second two-dimensional array (A2) of biological results. For illustration purposes, the arrays A1 and A2 may take the following format:

| | A1 | | | |
|---|---|---|---|---|
| | Ligand (L) | Ligand + Comp 1 | Ligand + Comp 2 | ... | Ligand + Comp M |
| Cell 1 | 0.50 | 0.40 | 0.30 | | 0.30 |
| Cell 2 | 1.80 | 2.90 | 0.40 | | 5.00 |
| ... | | | | | |
| Cell N | 0.10 | 0.10 | 0.00 | | 0.20 |

| | A2 | | | |
|---|---|---|---|---|
| | Small Mol (SM) | SM + Comp 1 | SM + Comp 2 | ... | SM + Comp M |
| Cell 1 | 0.40 | 0.30 | 0.35 | | 0.40 |
| Cell 2 | 1.20 | 3.00 | 0.20 | | 4.00 |
| ... | | | | | |
| Cell N | 0.40 | 0.20 | 0.20 | | 0.40 |

In a fifth step of the method according to the present invention, arrays A1 and A2 are normalized in such a way that each biological effect is expressed as its ratio to the largest biological effect observed in each of the different cells, leading to derived arrays B1 and B2.

These normalized, two-dimensional arrays 81 and 82 may take the following format:

| | B1 | | | |
|---|---|---|---|---|
| | Ligand (L) | Ligand + Comp 1 | Ligand + Comp 2 | ... | Ligand + Comp M |
| Cell 1 | 0.17 | 0.14 | 0.10 | | 0.10 |
| Cell 2 | 0.62 | 1.00 | 0.14 | | 1.72 |
| ... | | | | | |
| Cell N | 0.03 | 0.03 | 0.00 | | 0.07 |

| | B2 | | | |
|---|---|---|---|---|
| | Small Mol (SM) | SM + Comp 1 | SM + Comp 2 | ... | SM + Comp M |
| Cell 1 | 0.10 | 0.08 | 0.09 | | 0.10 |
| Cell 2 | 0.30 | 0.75 | 0.05 | | 1.00 |
| ... | | | | | |
| Cell N | 0.10 | 0.05 | 0.05 | | 0.10 |

In a sixth step of the method according to the present invention, the similarity between the array B1 and B2 is established. There are many customary mathematical algorithms to calculate such similarity, these algorithms are not part of the present invention but can be derived from any state-of-the-art mathematical textbook or established software tools to assess the similarity of gene expression profiles. Also different similarity indexes may be used to calculate such similarity such as for example the Cosine, Dice, Euclid, Forbes Hammen, Jaccard, Kulczynski, Manhattan, Pearson, Rogers-Tanimoto, Russel-Rao, Simpson, Tanimoto or Yule coefficient described in (J. D. Holliday et al., Combinatorial Chemistry and High Throughput Screening 2002, 5: 155-166).

As an intermediate step of this calculation we may obtain a one-dimensional similarity array (S) from which the similarity against each cell line may be determined:

| S | similarity |
|---|---|
| Cell 1 | 0.96 |
| Cell 2 | 0.65 |
| ... | |
| Cell N | 0.960 |

If the calculated similarity is higher than a predefined threshold, the small molecule may be considered as a true receptor ligand mimetic, to be used as a therapeutic agent. This predefined threshold can be determined either by measuring a small molecule that is known to have biological activity, but not being a receptor ligand.

In addition, the method according to this invention also delivers therapeutically useful combinations of small molecules that may act synergistically in diseases where the modulation of said receptor provides a therapeutic effect.

The present invention also refers to therapeutically useful treatments, diagnostic methods and compositions containing AP-121 as a CH-11 FAS receptor ligand mimetic, either alone or in combination with other therapeutically useful compounds and methods to establish their therapeutic utility. Preferably, the compositions of the present invention are orally applicable pharmaceutical dosage forms, particularly preferably solid dosage forms such as tablets, pills, capsules, and granules. In addition, and different to CH-11, AP-121 delivers therapeutic benefit to patients when compared to CH-11 or a similar anti-body since it is orally bioavailable and well tolerated (P. Drings of al., *Onkologie* 1992, 15: 375-382).

The invention is further described by the following figures and examples, which are solely for the purpose of illustrating specific embodiments of this invention, and are not to be construed as limiting the scope of the invention in any way. Materials used in tests below are either commercially available or easily prepared from commercially available materials by those skilled in the art.

FIGURES

FIG. 2. Depicts the in vivo effects of 1-O-octadecyl-2-O-methyl-glycero-3-phosphocholine (30 mg/kg body weight/day administered intraperitoneally for 15 days; FIG. 2A), (ionizing) radiation (absorbed dose of 5 Gray units administered on day 7); FIG. 2C), and a combination thereof (FIG. 2B) on LNCaP cells grown orthotopically in the prostates of nude mice (seven mice/group). Tumor growth was assessed via determining the serum level of the prostate-specific antigen (PSA) using a commercially available test kit as well as the tumor volume by means of magnetic resonance imaging. Graphed lines show tumor size in individual mice.

EXAMPLES AND EXPERIMENTAL PROCEDURES

Example 1

Selection Step

To demonstrate the practical utility of the method, we have chosen as one example the FAS receptor for which an activating small ligand is sought, the agonistic anti-body CH-11 as a suitable receptor ligand as well as AP-121 as a putative CH-11 mimetic. The known drugs Camptothecin, Temozolamide, Adriamycin and Tarceva were chosen as the panel of additional compounds for the combination measurements.

As a biological test panel, we selected the brain tumor cell lines U87MG, A172, LN-18, LN-229, U118MG, and T98G that have different levels of mutations in p53 and PTEN as well as FAS receptor expression:

| # | Cell Line | p53 | pTEN | FasL | Fas | ATCC # |
|---|---|---|---|---|---|---|
| 1 | U87 | wt | mut. (deletion) | + | wt | HTB-14 |
| 2 | A172 | wt | mut. (deletion) | + | wt | CRL-1620 |
| 3 | LN18 | mut | wt | + | wt | CRL-2610 |
| 4 | LN299 | mut | wt | + | wt | CRL-2611 |
| 5 | T98G | mut | mut. (deletion) | + | wt | CRL-1690 |
| 6 | U-118MG | mut | mut. (deletion) | ? | wt | HTB-15 |

Fas death receptors have been identified in most glioblastoma cells and expression levels correspond to the grade of tumor malignancy (O. Tachibana et al., *Cancer Res.* 1995, 55: 5528-30). Apoptosis and survival in high-grade astrocytomas as related to tumor Fas (APO-1/CD95) expression (Frankel et al., *Neurooncol.* 2002, 59: 27-34).

Protein expression of Fas receptor, Fas ligand (FasL), Bcl-2 and TGFh2 correlates with survival in initial and recurrent human gliomas (R. J. Strege et al., *J. Neurooncol.* 2004, 67: 29-39). Co-expression of Fas and Fas ligand has been described in malignant glial tumors and cell lines (N. Husain, et al. *Acta Neuropathol. (Berl)* 1998, 95: 287-90).

However, because the majority of glioblastoma cells are resistant to apoptosis induced by Fas ligand, harnessing the death-inducing pathway in gliomas will require sensitization by other means: ex vivo pediatric brain tumors express Fas (CD95) and FasL (CD95L) and are resistant to apoptosis induction. (C. D. Riffkin et al., *Proc. Natl. Acad. Sci. USA* 1999, 96: 14871-14876). Tumor Fas (APO-1/CD95) up-regulation results in increased apoptosis and survival times for rats with intracranial malignant gliomas (B. Frankel et al., *Neurosurgery* 2001, 49: 168-75).

The activating human anti-Fas anti-body clone CH-11 from Upstate Biotechnology, Lake Placid, N.Y., USA (Catalog #05-201) mouse immunoaffinity purified IgM; the antibody recognizes Fas (43 kD) and has cytolytic activity on human cells that express Fas. Murine WR19L and L929 cells transfected with cDNA encoding human FasL undergo apoptosis in response to the antibody. The antibody does not recognize TNF and does not cross-react with mouse FasL. After 24 h 86% of human Jurkat cells are killed.

In a seminal paper (A, Algeciras-Schimnich et al., *Proc. Natl. Acad. Sci. USA* 2003, 100: 11445-50), human cell lines were classified as type II if the soluble FasL was cytotoxic or as type I if it was not. However, CH-11, different to soluble FasL, is also cytotoxic to some type II cells. Both FasL and CH-11 can exert a synergistic activity on cells.

Therefore we concluded that finding a small molecule that is a mimetic of CH-11 could be of therapeutic use in situations where tumor cells are not sensitive at all or not sensitive enough against endogenous FasL or in situations when not sufficient FasL is expressed in the diseased tissue.

Example 2

Cell Lines and Reagents

U-118 MG (glioblastoma/astrocytoma, p53 mut, PTEN mut), T98G (glioblastoma multiforme, p53 mut, PTEN mut), A172 (glioblastoma, p53 w.t., PTEN mut) and U87 MG (glioblastoma/astrocytoma p53 w.t., PTEN mut) were purchased from ATCC.

U-118 MG and A172 were incubated in DMEM media supplemented with 10% FBS and PIS, T98G and U87 MG were incubated in MEM media supplemented with 0.1 mM of non-essential amino acids solution (Gibco), 10% FBS and P/S according to ATCC recommendations. AP-121 was prepared as 5 mM stock solution in distilled sterile water, Temozolomide (TMZ) (Haorui Pharma-Chem, Inc., Edison, N.J.) was prepared as 100 mM in sterile filtrated DMSO; Adriamycin (ADR) (Sigma) was prepared as 1 mM in distilled sterile water; Camptothecin (CTP) (Sigma) was prepared as 10 mM solution in 0.1 N NaOH; Tarceva (Proteinkinase, Germany) was prepared as 5 mM solution in sterile DMSO. All compound stocks were kept at −20° C.

Example 3

WST-1 Proliferation Assay 2000 cells were plated in each well of 96-well flat bottom plates, and incubated overnight at 370C in 5% CO2. The growth of plated cells was measured by adding 7.5 µM of WST-1 reagent (Roche Applied Sciences, Germany) to 3 control wells and measuring the absorbance at 650 nm and at 450 nm, respectively, with a SpectraMax250 plate reader. If the OD650-OD450 values were above 0.5, the remainder of the plate was used for incubation with AP-121, other pharmacological agents or solvent control for 96 hours.

After this incubation, VVST-1 reagent was added to the wells and OD650-OD450 values were calculated as before. six wells were assayed for each conditions and standard deviation was determined: all experiments were performed at least three times independently. After elucidation of individual IC50 values for each compound, the simultaneous combination treatment of AP-121 and the chemotherapeutic agent at their IC50 ratio was performed; combination index (CI) was determined by Calcusyn software package (Biosoft, Ferguson, Mo.). Data were evaluated by calculating the means of the combination index (CI), where a CI of <0.3 indicates a strong synergistic effect, 0.3<CI<0.7 a synergistic effect, 0.7<CI<0.9 moderate synergy, 0.9<CI<1 additive effect and CI>1 antagonistic effect, respectively.

For the AP-121 cell proliferation drug combination measurements, the ED50 was determined for each drug. Six different concentrations of each drug were used in combinations index measurements and compared to +/− cells, and compared to controls without compound. Each combination was repeated 6 times at 2 different time points (24 and 96 hours), each of the above experiments was repeated 3 times to obtain valid results.

For example, one such measurement is shown below, with the U118 cell line, and a mixture of AP-121 and Temozolamide (TMZ), measured as the optical absorption difference at 450 versus 650 nm. The upper two rows denote the micromolar concentrations of AP-121 or TMZ in six different ratios, row A contains the media with compounds but not adding cells, row B to G cells and the respective compound mixture is added, row H1-H3 are with cells but without the compound mixture, adding water instead of the compound mixture, H4-H6 is the same as H1-H3 but with water containing 1% DMSO, WST reagent is added to all wells with exception of H1-H3.

|   | AP-121 | | | | | |
|---|---|---|---|---|---|---|
|   | 20 | 10 | 5 | 2.5 | 1.25 | 0.625 |
|   | TMZ | | | | | |
|   | 1000 | 500 | 250 | 125 | 62.5 | 31.2500 |
| A | 0.172 | 0.19 | 0.183 | 0.184 | 0.191 | 0.201 |
| B | 0.22 | 0.309 | 0.368 | 0.362 | 0.457 | 0.494 |
| C | 0.229 | 0.322 | 0.39 | 0.383 | 0.451 | 0.437 |
| D | 0.251 | 0.339 | 0.397 | 0.418 | 0.461 | 0.478 |
| E | 0.253 | 0.333 | 0.421 | 0.424 | 0.417 | 0.482 |
| F | 0.254 | 0.322 | 0.384 | 0.426 | 0.456 | 0.475 |
| G | 0.258 | 0.327 | 0.4 | 0.392 | 0.447 | 0.444 |
| H | 0.896 | 0.926 | 0.97 | 0.39 | 0.383 | 0.398 |

From this experiment, and the previously determined ED50 of each individual compound against each cell line, the combination index was calculated as shown below in the Experimental Summary for each compound mixture and cell line using the Calcusyn program.

EXPERIMENTAL SUMMARY: In the following only some selected data of the full experiment are described.

Example 4

AP-121 Combination Indexes (CI)

| COMBINATION | CI Values at | | | | | |
|---|---|---|---|---|---|---|
| | ED50 | ED75 | ED90 | MEAN | | |
| Date: Aug. 15, 2006 CELL LINE U87MG glioblastoma/astrocytoma: p53 wt, pTEN mut | | | | | | |
| AP-121-TMZ (1:40) | 0.477 | 0.418 | 0.396 | 0.431 | CI < 0.5 | STRONG SYNERGY |
| AP-121-CPT (250:1) | 0.849 | 0.652 | 0.502 | 0.668 | 0.5 < CI < 0.75 | SYNERGY |
| AP-121-ADR (100:1) | 0.945 | 0.695 | 0.536 | 0.725 | 0.5 < CI < 0.75 | SYNERGY |
| AP-121-Tarceva (2:1) | 1.610 | 1.985 | 2.460 | 2.018 | CI > 1.0 | ANTAGONISM |
| AP-121-CH-11 (1:100) | 1.328 | 1.888 | 2.684 | 1.967 | CI > 1.0 | ANTAGONISM |
| Date: Aug. 24, 2006 CELL LINE U87MG glioblastoma/astrocytoma: p53 wt, pTEN mut | | | | | | |
| AP-121-TMZ (1:50) | 0.608 | 0.702 | 0.838 | 0.716 | 0.5 < CI < 0.75 | SYNERGY |
| AP-121-CPT (200:1) | 1.057 | 0.608 | 0.378 | 0.681 | 0.5 < CI < 0.75 | SYNERGY |
| AP-121-ADR (50:1) | 0.525 | 0.447 | 0.470 | 0.481 | CI < 0.5 | STRONG SYNERGY |
| AP-121-Tarceva (1:2) | 1.448 | 1.103 | 0.934 | 1.162 | CI > 1.0 | ANTAGONISM |
| Date: Sep. 07, 2006 CELL LINE U87MG glioblastoma/astrocytoma: p53 wt, pTEN mut | | | | | | |
| AP-121-TMZ (1:50) | 0.311 | 0.485 | 0.870 | 0.555 | 0.5 < CI < 0.75 | SYNERGY |
| AP-121-CPT (250:1) | 2.076 | 2.269 | 2.579 | 2.308 | CI > 1.0 | ANTAGONISM |
| AP-121-ADR (50:1) | 0.671 | 0.857 | 1.098 | 0.875 | CI < 0.5 | SYNERGY |
| AP-121-Tarceva (1:2) | 2.122 | 2.550 | 3.248 | 2.640 | CI > 1.0 | ANTAGONISM |
| Date: Aug. 15, 2006 CELL LINE A172 glioblastoma: p53 wt, pTEN mut | | | | | | |
| AP-121-TMZ (1:10) | 0.659 | 0.216 | 0.073 | 0.316 | CI < 0.5 | STRONG SYNERGY |
| AP-121-CPT (250:1) | 0.554 | 0.378 | 0.284 | 0.405 | CI < 0.5 | STRONG SYNERGY |
| AP-121-ADR (50:1) | 0.622 | 0.472 | 0.402 | 0.499 | CI < 0.5 | STRONG SYNERGY |
| AP-121-Tarceva (1:5) | 1.157 | 0.662 | 0.406 | 0.742 | 0.5 < CI < 0.75 | SYNERGY |
| AP-121-CH-11 (1:200) | 0.260 | 0.357 | 0.529 | 0.382 | CI < 0.5 | STRONG SYNERGY |
| Date: Aug. 24, 2006 CELL LINE A172 glioblastoma: p53 wt, pTEN mut | | | | | | |
| AP-121-TMZ (1:10) | 0.602 | 0.360 | 0.238 | 0.400 | CI < 0.5 | STRONG SYNERGY |
| AP-121-CPT (250:1) | 0.634 | 0.492 | 0.382 | 0.503 | CI < 0.5 | STRONG SYNERGY |
| AP-121-ADR (50:1) | 1.410 | 1.013 | 0.734 | 1.052 | CI = 1.0 | ADDITIVE |
| AP-121-Tarceva (1:2) | 0.971 | 0.628 | 0.407 | 0.669 | 0.5 < CI < 0.75 | SYNERGY |
| Date: Sep. 07, 2006 CELL LINE A172 glioblastoma: p53 wt, pTEN mut | | | | | | |
| AP-121-TMZ (1:10) | 0.529 | 0.463 | 0.480 | 0.491 | CI < 0.5 | STRONG SYNERGY |
| AP-121-CPT (250:1) | 0.893 | 0.874 | 0.872 | 0.880 | CI < 0.5 | SYNERGY |
| AP-121-ADR (50:1) | 0.770 | 0.767 | 0.775 | 0.771 | CI < 0.5 | SYNERGY |
| AP-121-Tarceva (1:5) | 0.612 | 0.589 | 0.588 | 0.596 | 0.5 < CI < 0.75 | SYNERGY |

| COMBINATION | CI Values at | | | | | |
|---|---|---|---|---|---|---|
| | ED50 | ED75 | ED90 | MEAN | | |

Date: Aug. 15, 2006
CELL LINE U118MG glioblastoma/astrocytoma: p53 mut, pTEN mut

| COMBINATION | ED50 | ED75 | ED90 | MEAN | | |
|---|---|---|---|---|---|---|
| AP-121-TMZ (1:40) | 0.756 | 0.595 | 0.560 | 0.637 | 0.5 < CI < 0.75 | SYNERGY |
| AP-121-CPT (2500:1) | 0.541 | 16.227 | 613.210 | 209.992 | CI > 1.0 | ANTAGONISM |
| AP-121-ADR (100:1) | 0.380 | 0.766 | 1.793 | 0.980 | CI = 1.0 | ADDITIVE |
| AP-121-Tarceva (1:2) | 0.598 | 0.408 | 0.336 | 0.448 | CI < 0.5 | STRONG SYNERGY |
| AP-121-CH-11 (1:100) | 0.561 | 1.038 | 2.089 | 1.230 | CI > 1.0 | ANTAGONISM |

Date: Aug. 24, 2006
CELL LINE U118MG glioblastoma/astrocytoma: p53 mut, pTEN mut

| COMBINATION | ED50 | ED75 | ED90 | MEAN | | |
|---|---|---|---|---|---|---|
| AP-121-TMZ (1:50) | 0.637 | 0.450 | 0.514 | 0.534 | 0.5 < CI < 0.75 | SYNERGY |
| AP-121-CPT (2000:1) | 1.178 | 1.805 | 4.051 | 2.345 | CI > 1.0 | ANTAGONISM |
| AP-121-ADR (50:1) | 0.804 | 0.381 | 0.222 | 0.469 | CI < 0.5 | STRONG SYNERGY |
| AP-121-Tarceva (1:2) | 2.498 | 1.561 | 1.717 | 1.925 | CI > 1.0 | ANTAGONISM |

Date: Sep. 07, 2006
CELL LINE U118MG glioblastoma/astrocytoma: p53 mut, pTEN mut

| COMBINATION | ED50 | ED75 | ED90 | MEAN | | |
|---|---|---|---|---|---|---|
| AP-121-TMZ (1:50) | 0.578 | 0.462 | 0.381 | 0.474 | CI < 0.5 | STRONG SYNERGY |
| AP-121-CPT (1000:1) | 1.644 | 1.996 | 2.446 | 2.028 | CI > 1.0 | ANTAGONISM |
| AP-121-ADR (50:1) | 1.231 | 1.025 | 0.857 | 1.038 | CI = 1.0 | ADDITIVE |
| AP-121-Tarceva (1:5) | 1.391 | 0.949 | 0.677 | 1.005 | CI = 1.0 | ADDITIVE |

Date: Aug. 24, 2006
CELL LINE LN-18 glioblastoma: p53 mut, pTEN wt

| COMBINATION | ED50 | ED75 | ED90 | MEAN | | |
|---|---|---|---|---|---|---|
| AP-121-TMZ (1:50) | 4.735 | 5.368 | 6.090 | 5.397 | CI > 1.0 | ANTAGONISM |
| AP-121-CPT (10:1) | 29.352 | 16.143 | 9.274 | 18.256 | CI > 1.0 | ANTAGONISM |
| AP-121-ADR (5:1) | 1.944 | 2.691 | 3.732 | 2.789 | CI > 1.0 | ANTAGONISM |
| AP-121-Tarceva (1:10) | 6.529 | 6.744 | 7.022 | 6.765 | CI > 1.0 | ANTAGONISM |

Date: Sep. 07, 2006
CELL LINE LN-18 glioblastoma: p53 mut, pTEN wt

| COMBINATION | ED50 | ED75 | ED90 | MEAN | | |
|---|---|---|---|---|---|---|
| AP-121-TMZ (1:100) | 1.026 | 1.030 | 1.043 | 1.033 | CI = 1.0 | ADDITIVE |
| AP-121-CPT (20:1) | 1.146 | 1.073 | 1.022 | 1.080 | CI > 1.0 | ADDITIVE |
| AP-121-ADR (10:1) | 1.235 | 1.188 | 1.147 | 1.190 | CI > 1.0 | ANTAGONISM |
| AP-121-Tarceva (1:20) | 1.589 | 1.684 | 1.990 | 1.754 | CI > 1.0 | ANTAGONISM |

Example 5

CH-11 Combination Indexes

| COMBINATION | CI Values at | | | | | |
|---|---|---|---|---|---|---|
| | ED50 | ED75 | ED90 | MEAN | | |

Date: Sep. 01, 2006
CELL LINE U87MG glioblastoma/astrocytoma: p53 wt, pTEN mut

| COMBINATION | ED50 | ED75 | ED90 | MEAN | | |
|---|---|---|---|---|---|---|
| CH-11/TMZ (1:100) | 0.015 | 0.006 | 0.004 | 0.008 | CI < 0.5 | STRONG SYNERGY |

-continued

| COMBINATION | CI Values at | | | | | |
|---|---|---|---|---|---|---|
| | ED50 | ED75 | ED90 | MEAN | | |
| CH-11/CPT (71:1) | 0.247 | 0.141 | 0.201 | 0.196 | CI < 0.5 | STRONG SYNERGY |
| CH-11/ADR (10:1) | 0.326 | 0.305 | 0.485 | 0.372 | CI < 0.5 | STRONG SYNERGY |
| CH-11/Tarceva (1:2.5) | 0.144 | 0.071 | 0.076 | 0.097 | CI < 0.5 | STRONG SYNERGY |

Date: Aug. 24, 2006
CELL LINE A172 glioblastoma: p53 wt, pTEN mut

| CH-11/TMZ (1:8) | 0.125 | 0.126 | 0.151 | 0.134 | CI < 0.5 | STRONG SYNERGY |
| CH-11/CPT (143:1) | 0.872 | 2.992 | 10.439 | 4.768 | CI > 1.0 | ANTAGONISM |
| CH-11/ADR (26:1) | 0.831 | 1.430 | 2.477 | 1.579 | CI > 1.0 | ANTAGONISM |
| CH-11/Tarceva (1:8) | 0.608 | 0.636 | 0.683 | 0.643 | 0.5 < CI < 0.75 | SYNERGY |

Date: Sep. 01, 2006
CELL LINE A172 glioblastoma: p53 wt, pTEN mut

| CH-11/TMZ (1:8) | 0.046 | 0.055 | 0.079 | 0.060 | CI < 0.5 | STRONG SYNERGY |
| CH-11/CPT (143:1) | 1.049 | 1.475 | 2.110 | 1.545 | CI > 1.0 | ANTAGONISM |
| CH-11/ADR (26:1) | 1.629 | 3.368 | 7.003 | 4.000 | CI > 1.0 | ANTAGONISM |
| CH-11/Tarceva (1:8) | 0.272 | 0.310 | 0.361 | 0.314 | CI < 0.5 | STRONG SYNERGY |

Date: Sep. 01, 2006
CELL LINE U118MG glioblastoma/astrocytoma: p53 mut pTEN mut

| CH-11/TMZ (1:100) | 5.723 | 10.152 | 19.618 | 11.831 | CI > 1.0 | ANTAGONISM |
| CH-11/CPT (30:1) | 7.937 | 6.804 | 6.764 | 7.168 | CI > 1.0 | ANTAGONISM |
| CH-11/ADR (10:1) | 0.612 | 0.166 | 0.102 | 0.293 | CI < 0.5 | STRONG SYNERGY |
| CH-11/Tarceva (1:8) | 0.708 | 0.163 | 0.144 | 0.338 | CI < 0.5 | STRONG SYNERGY |

In a further analysis, the following $IC_{50}$ (μM) values were determined for the different AP-121 combinations employed.

| Cell line | AP-121 | CPT | TMZ | ADR | CH11 | Tarceva | Mutation Status |
|---|---|---|---|---|---|---|---|
| U87MG | 8.5 | 0.04 | 425.2 | 0.11 | 854 | 5.9 | p53wt, pTEN-mut |
| A172 | 4.6 | 0.02 | 38.3 | 0.07 | >1000 | 18.8 | p53wt, pTEN-mut |
| LN-18 | 1.3 | 0.04 | 553.5 | 0.09 | <31.25 | 20 | p53mut, pTEN-wt |
| LN-229 | 4.3 | 0.02 | 278.4 | 0.13 | 521.5 | 3.9 | p53mut, pTEN-wt |
| U118MG | 3.6 | 0.004 | 381.5 | 0.12 | 490.7 | 18.8 | p53mut, pTEN-mut |
| T98G | 4.1 | 0.02 | 608.3 | 0.17 | 517.8 | 14.4 | p53mut, pTEN-mut |

For the calculation of the IC50 values the AP-121 combinations administered to the respective cell lines were as follows:

| U87MG combinations | | | | | | |
|---|---|---|---|---|---|---|
| | AP-121/ | | | | | |
| Compound | 1 AP-121 | 250:1 CPT | 1:40 TMZ | 100:1 ADR | 1:100 CH11 | 2:1 Tarceva |
| 6 | 0.625 | 0.0025 | 25 | 0.00625 | 62.5 | 0.3125 |
| 5 | 1.25 | 0.005 | 50 | 0.0125 | 125 | 0.625 |
| 4 | 2.5 | 0.01 | 100 | 0.025 | 250 | 1.25 |
| 3 | 5 | 0.02 | 200 | 0.05 | 500 | 2.5 |
| 2 | 10 | 0.04 | 400 | 0.1 | 1000 | 5 |
| 1 | 20 | 0.08 | 800 | 0.2 | 2000 | 10 |

| A172 combinations | | | | | | |
|---|---|---|---|---|---|---|
| | AP-121/ | | | | | |
| Compound | 1 AP-121 | 250:1 CPT | 1:10 TMZ | 50:1 ADR | 1:200 CH11 | 1:5 Tarceva |
| 6 | 0.3125 | 0.00125 | 3.125 | 0.00625 | 62.5 | 1.5625 |
| 5 | 0.625 | 0.0025 | 6.25 | 0.0125 | 125 | 3.125 |
| 4 | 1.25 | 0.005 | 12.5 | 0.025 | 250 | 6.25 |
| 3 | 2.5 | 0.01 | 25 | 0.05 | 500 | 12.5 |
| 2 | 5 | 0.02 | 50 | 0.1 | 1000 | 25 |
| 1 | 10 | 0.04 | 100 | 0.2 | 2000 | 50 |

LN-18 combinations

| Compound | 1<br>AP-121 | 20:1<br>AP-121/<br>CPT | 1:100<br>TMZ | 10:1<br>ADR | 1:100<br>CH11 | 1:20<br>Tarceva |
|---|---|---|---|---|---|---|
| 6 | 0.15625 | 0.00781 | 15.625 | 0.01562 | 31.25 | 3.125 |
| 5 | 0.3125 | 0.01562 | 31.25 | 0.03125 | 62.5 | 6.25 |
| 4 | 0.625 | 0.03125 | 62.5 | 0.0625 | 125 | 12.5 |
| 3 | 1.25 | 0.0625 | 125 | 0.125 | 250 | 25 |
| 2 | 2.5 | 0.125 | 250 | 0.25 | 500 | 50 |
| 1 | 5 | 0.25 | 500 | 0.5 | 1000 | 100 |

LN-229 combination

| Compound | 1<br>AP-121 | 200:1<br>AP-121/<br>CPT | 1:50<br>TMZ | 50:1<br>ADR | 1:100<br>CH11 | 1:1<br>Tarceva |
|---|---|---|---|---|---|---|
| 6 | 0.3125 | 0.00156 | 15.625 | 0.00625 | 31.25 | 0.3125 |
| 5 | 0.625 | 0.00313 | 31.25 | 0.0125 | 62.5 | 0.625 |
| 4 | 1.25 | 0.00625 | 62.5 | 0.025 | 125 | 1.25 |
| 3 | 2.5 | 0.0125 | 125 | 0.05 | 250 | 2.5 |
| 2 | 5 | 0.025 | 250 | 0.1 | 500 | 5 |
| 1 | 10 | 0.05 | 500 | 0.2 | 1000 | 10 |

U118MG combination

| Compound | 1<br>AP-121 | 2500:1<br>AP-121/<br>CPT | 1:40<br>TMZ | 100:1<br>ADR | 1:50<br>CH11 | 1:2<br>Tarceva |
|---|---|---|---|---|---|---|
| 6 | 0.625 | 0.00025 | 25 | 0.00625 | 31.25 | 1.25 |
| 5 | 1.25 | 0.0005 | 50 | 0.0125 | 62.5 | 2.5 |
| 4 | 2.5 | 0.001 | 100 | 0.025 | 125 | 5 |
| 3 | 5 | 0.002 | 200 | 0.05 | 250 | 10 |
| 2 | 10 | 0.004 | 400 | 0.1 | 500 | 20 |
| 1 | 20 | 0.008 | 800 | 0.2 | 1000 | 40 |

T98G combination

| Compound | 1<br>AP-121 | 200:1<br>AP-121/<br>CPT | 1:100<br>TMZ | 25:1<br>ADR | 1:100<br>CH11 | 1:5<br>Tarceva |
|---|---|---|---|---|---|---|
| 6 | 0.3125 | 0.0015625 | 31.25 | 0.0125 | 31.25 | 1.5625 |
| 5 | 0.625 | 0.003125 | 62.5 | 0.025 | 62.5 | 3.125 |
| 4 | 1.25 | 0.00625 | 125 | 0.05 | 125 | 6.25 |
| 3 | 2.5 | 0.0125 | 250 | 0.1 | 250 | 12.5 |
| 2 | 5 | 0.025 | 500 | 0.2 | 500 | 25 |
| 1 | 10 | 0.05 | 1000 | 0.4 | 1000 | 50 |

Summary: Synergy of AP-121 with additional compounds in respect to mutational status of the used cells

| AP121-combinations | p53 | PTEN | cell line |
|---|---|---|---|
| 1 Synergy/additive | w.t. | mut | U87MG, A172 |
| 2 Synergy/additive/antagonistic | mut | mut | U118MG, T98G |
| 3 Antagonistic | mut | w.t. | LN229, LN18 |

Example 6

Array of Biological ED50 Data for the Receptor Ligand and the Small Molecule

From this data the following data arrays A2 and A1 can be derived using the respective ED50 data for AP-121 and the corresponding compound mixtures:

| | ED50, μM | | | | |
|---|---|---|---|---|---|
| Cells | AP-121 | CPT + AP121 | TMZ + AP121 | ADR + AP121 | Tarceva + AP121 |
| U87MG | 6.8 | 0.016 | 75.3 | 0.04 | 4.9 |
| A172 | 4.2 | 0.009 | 9.3 | 0.04 | 9.6 |
| U118MG | 4.8 | 0.002 | 176 | 0.04 | 15.5 | and for CH-11:

| | ED50, μM | | | | |
|---|---|---|---|---|---|
| Cells | CH11 | CPT + CH11 | TWZ + CH11 | ADR + CH11 | Tarceva + CH11 |
| U87MG | 854 | 0.007 | 4.1 | 0.026 | 0.54 |
| A172 | 1055 | 0.007 | 1.7 | 0.025 | 3.3 |
| U118MG | 320.6 | 0.004 | 83.6 | 0.02 | 4.6 |

Consequently, the normalized arrays B2:

| | ED50, μM | | | | |
|---|---|---|---|---|---|
| Cells | AP-121 | CPT + AP121 | TMZ + AP121 | ADR + AP121 | Tarceva + AP121 |
| U87MG | 1.00 | 1.00 | 0.43 | 1.00 | 0.32 |
| A172 | 0.62 | 0.56 | 0.05 | 1.00 | 0.62 |
| U118MG | 0.71 | 0.13 | 1.00 | 1.00 | 1.00 | and B1 are calculated:

| | ED50, μM | | | | |
|---|---|---|---|---|---|
| Cells | CH11 | CPT + CH11 | TMZ + CH11 | ADR + CH11 | Tarceva + CH11 |
| U87MG | 0.81 | 1.00 | 0.05 | 1.00 | 0.12 |
| A172 | 1.00 | 1.00 | 0.02 | 0.96 | 0.72 |
| U118MG | 0.30 | 0.57 | 1.00 | 0.77 | 1.00 |

From B1 and B2 a similarity array S can be calculated by simply averaging the similarity values for each compound or compound mixture per cell,

| Cells/ED50, μM | similarity |
|---|---|
| U87MG | 0.85 |
| A172 | 0.80 |
| U118MG | 0.78 |
| total similarity: | 0.81 | where a similarity value of 1.00 corresponds to the highest similarity possible and 0.00 to the lowest possible overlap of biological activity.

Overall, the data from example 6 demonstrates that by using the method according to the present invention, a specific agonistic antibody against Fas receptor CH-11 as a selective receptor ligand and AP-121 as a small molecule putative receptor ligand mimetic, as well as several additional compounds in the respective compound mixtures, it can be shown that the biological effect of AP-121 is similar to the one exerted by CH-11.

The same evaluation method can also be applied to the arrays of combination indexes from example 4 and 5 instead of the ED50's as biological effects, which delivers a high similarity value of about 0.6 between CH-11 and AP-121.

In addition, a strong synergistic effect was observed in all three cell lines together with temozolamide, the current standard therapy for glioblastoma multiforme and anaplastic astrocytoma.

Example 7

Using the procedure outlined in example 4 and 5, a strong synergistic effect was observed also for cisplatinum (DDP)/AP-121 and gemicitabin (GMZ)/AP-121 in non-small lung cancer cell lines. DDP and GMZ were both purchased from Sigma-aldrich Corp., St. Louis, Mo., USA. The following cell lines were used: A549 (FAS negative), NCI-H460 (FAS positive), and HCC827 (FAS positive), all obtained from the ATTC, Rockville, Md., USA.

| CI | Ratio | A549 ED50 | ED75 | ED90 | CI-mean | Effect | IC50 µM AP-121 | GMZ | DDP |
|---|---|---|---|---|---|---|---|---|---|
| AP-121-GMZ combi | 2500:1 | 1.778 | 1.542 | 1.343 | 1.6 | Antagonism | 8 | 0.009 | |
| AP-121-GMZ combi | 5000:1 | 48.906 | 18.706 | 7.465 | 25.0 | Antagonism | 6 | 0.0006 | |
| AP-121-GMZ combi | 1000:1 | 200.939 | 68.248 | 23.399 | 97.5 | Antagonism | | | |
| AP-121-96h-GMZ-48h | 2000:1 | 0.721 | 0.642 | 0.576 | 0.65 | Synergism | | | |
| GMZ-48h-AP-121-96h | 1:2000 | 0.290 | 0.286 | 0.284 | 0.29 | Strong Synergism | | | |
| AP-121-48h-GMZ-96h | 2000:1 | >100 | >100 | >100 | >100 | Antagonism | | | |
| GMZ-96h-AP-121-48h | 1:2000 | >100 | >100 | >100 | >100 | Antagonism | | | |
| AP-121-DDP combi | 1:3 | 54.199 | 217.923 | 886.111 | 386.1 | Antagonism | 8 | | 155.4 |
| AP-121-DDP combi | 1:5 | 0.231 | 0.386 | 0.652 | 0.42 | Strong Synergism | 6 | | 12.7 |
| AP-121-DDP combi | 1:10 | 0.200 | 0.336 | 0.570 | 0.37 | Strong Synergism | 6 | | 12.7 |
| AP-121-DDP combi | 1:5 | 0.582 | 0.665 | 0.761 | 0.67 | Synergism | 6.9 | | 3.8 |
| AP-121-DDP combi | 01:10 | 0.537 | 0.601 | 0.673 | 0.60 | Synergism | 6.9 | | 3.8 |

| CI | Ratio | NCI-H460 ED50 | ED75 | ED90 | CI-mean | Effect | IC50 µM AP-121 | GMZ | DDP |
|---|---|---|---|---|---|---|---|---|---|
| AP-121-GMZ combi | 20:1 | 7.954 | 5.736 | 4.182 | 6.0 | Antagonism | 1.5 | 0.003 | |
| AP-121-GMZ combi | 50:1 | 4.248 | 2.696 | 1.793 | 2.9 | Antagonism | 1.4 | 0.006 | |
| AP-121-GMZ combi | 250:1 | 2.002 | 1.605 | 1.391 | 1.7 | Antagonism | 1.4 | | |
| AP-121-96h-GMZ-48h | 100:1 | 0.660 | 0.728 | 0.851 | 0.75 | Synergism | | | |
| GMZ-48h-AP-121-96h | 1:100 | 0.193 | 0.334 | 0.611 | 0.38 | Strong Synergism | | | |
| AP-121-48h-GMZ-96h | 100:1 | 0.573 | 0.570 | 0.598 | 0.58 | Synergism | | | |
| GMZ-96h-AP-121-48h | 1:100 | 0.776 | 0.742 | 0.726 | 0.75 | Synergism | | | |
| AP-121-DDP combi | 1:3 | 1.966 | 2.138 | 2.325 | 2.1 | Antagonism | 1.5 | | 51.7 |
| AP-121-DDP combi | 1:5 | 2.650 | 1.870 | 1.368 | 2.0 | Antagonism | 1.4 | | 2.5 |
| AP-121-DDP combi | 1:10 | 2.372 | 1.785 | 1.373 | 1.8 | Antagonism | | | |

-continued

| | NCI-H460 | | | | | IC50 μM | | |
|---|---|---|---|---|---|---|---|---|
| CI | Ratio | ED50 | ED75 | ED90 | CI-mean | Effect | AP-121 | GMZ | DDP |
| AP-121-DDP combi | 1:5 | 0.860 | 0.822 | 0.786 | 0.82 | Synergism | 2 | | 1.3 |
| AP-121-DDP combi | 1:10 | 0.881 | 0.852 | 0.824 | 0.85 | Synergism | 2 | | 1.3 |

| | HCC827 | | | | | IC50 μM | | |
|---|---|---|---|---|---|---|---|---|
| CI | Ratio | ED50 | ED75 | ED90 | CI-mean | Effect | AP-121 | GMZ | DDP |
| AP-121-GMZ combi | 20:1 | 0.967 | 1.912 | 3.780 | 2.2 | Antagonism | 0.85 | 0.078 | |
| AP-121-GMZ combi | 10:1 | 19.894 | 2.935 | 0.493 | 7.8 | Antagonism | 1.6 | 0.002 | |
| AP-121-GMZ combi | 50:1 | 28.988 | 3.856 | 0.805 | 11.2 | Antagonism | 1.6 | | |
| AP-121-96h-GMZ-48h | 100:1 | 0.653 | 0.737 | 0.841 | 0.74 | Synergism | | | |
| GMZ-48h-AP-121-96h | 1:100 | 0.183 | 0.274 | 0.416 | 0.29 | Strong Synergism | | | |
| AP-121-48h-GMZ-96h | 100:1 | 1.072 | 0.964 | 0.870 | 0.97 | Additive | | | |
| GMZ-96h-AP-121-48h | 1:100 | 0.743 | 0.532 | 0.383 | 0.55 | Synergism | | | |
| AP-121-DDP combi | 1:5 | 2.696 | 3.172 | 3.735 | 3.2 | Antagonism | 0.85 | | >50 |
| AP-121-DDP combi | 1:10 | 0.668 | 0.668 | 0.667 | 0.67 | Synergism | 1.6 | | 3.4 |
| AP-121-DDP combi | 1:50 | 0.566 | 0.627 | 0.695 | 0.63 | Synergism | 1.6 | | 3.4 |
| AP-121-DDP combi | 1:10 | 1.348 | 1.150 | 0.981 | 1.16 | Antagonism | 2.4 | | 3.5 |
| AP-121-DDP combi | 1:50 | 0.190 | 0.251 | 0.331 | 0.26 | Strong Synergism | 2.4 | | 3.5 |

Example 8

It is known that prostate cancer cell lines express FAS receptor, that some of them are not sensitive to FAS (O. W. Rokhlin et al., Cancer Res. 1997, 57: 1758-68). LNCaP is a prostate cancer cell line that has reduced sensitivity to irradiation while the agonistic FAS anti-body CH-11 sensitizes cells to irradiation induced apoptosis (K. Kimura and E. P. Gelmann, Cell Death and Differentiation 2002, 9: 972-980; cf. also the following example). Therefore, we have performed animal experiments by injecting LNCaP cells into the prostate of mice and, after tumor growth, applied AP-121 with different doses of 0-30 mg/kg intraperitoneal injections and concomitant irradiation.

In the treated animals a dose-dependent effect was observed with the PSA (prostate specific antigen) levels being reduced after few days of treatment and shrinkage of the tumor size after one week of treatment, showing the effectivity of AP-121 to mimic the biological effect of the agonistic antibody CH-11 in an therapeutically relevant in vivo experiment.

Example 9

Effects of
1-O-octadecyl-2-O-methyl-glycero-3-phosphocholine
in the treatment of prostate cancer Prostate cancer is a type of cancer developing in the prostate, a gland in the male reproductive system. Prostate cancer is most often discovered by physical examination or by screening blood tests, such as the PSA (prostate specific antigen) test. The PSA test measures the blood level of prostate-specific antigen, a serine protease similar to kallikrein. Its normal function is to liquefy gelatinous semen after ejaculation, allowing spermatazoa to more easily navigate through the uterine cervix. PSA levels above about 4 ng/ml are generally considered indicative for a risk to develop prostate cancer. However, PSA is not a perfect test and should thus be corroborated by additional analyses such as the detection of cell-associated PCA-3 mRNA in the urine.

The two most common treatments for locally-advanced or high risk prostate cancer are radiation therapy (RT) and androgen deprivation (AD), that is hormonal therapy.

The effects of 1-O-octadecyl-2-O-methyl-glycero-3-phosphocholine alone and in combination with RT, AD or RT+AD on the extent of programmed cell death (apoptosis) and the survival of prostate cancer sells were investigated, respectively.

First, the in vitro effects of 1-O-octadecyl-2-O-methyl-glycero-3-phosphocholine, (ionizing) radiation, and a combination thereof on programmed cell death (apoptosis) and the survival rate of LNCaP androgen-sensitive human prostate adenocarcinoma cells were measured. The LNCaP cell line was established from a metastatic lesion of the adenocarcinoma. The cells were treated with a final concentration of 10 μM 1-O-octadecyl-2-O-methyl-glycero-3-phosphocholine and (ionizing) radiation corresponding to an absorbed dose of 5 Gray units.

Apoptosis was determined using the Apo-ONE™ Homogenous Caspase-3/7 Assay, Promega, Inc., Madison, VV1, USA according to the manufacturers instructions. The percentage of living tumor cells was estimated by means of trypan blue dye exclusion as described (Freshney, R. I. (1994) *Culture of Animal Cells: A Manual of Basic Technique.* 3rd Ed. Wiley-Liss. New York. USA)

Figure 1:
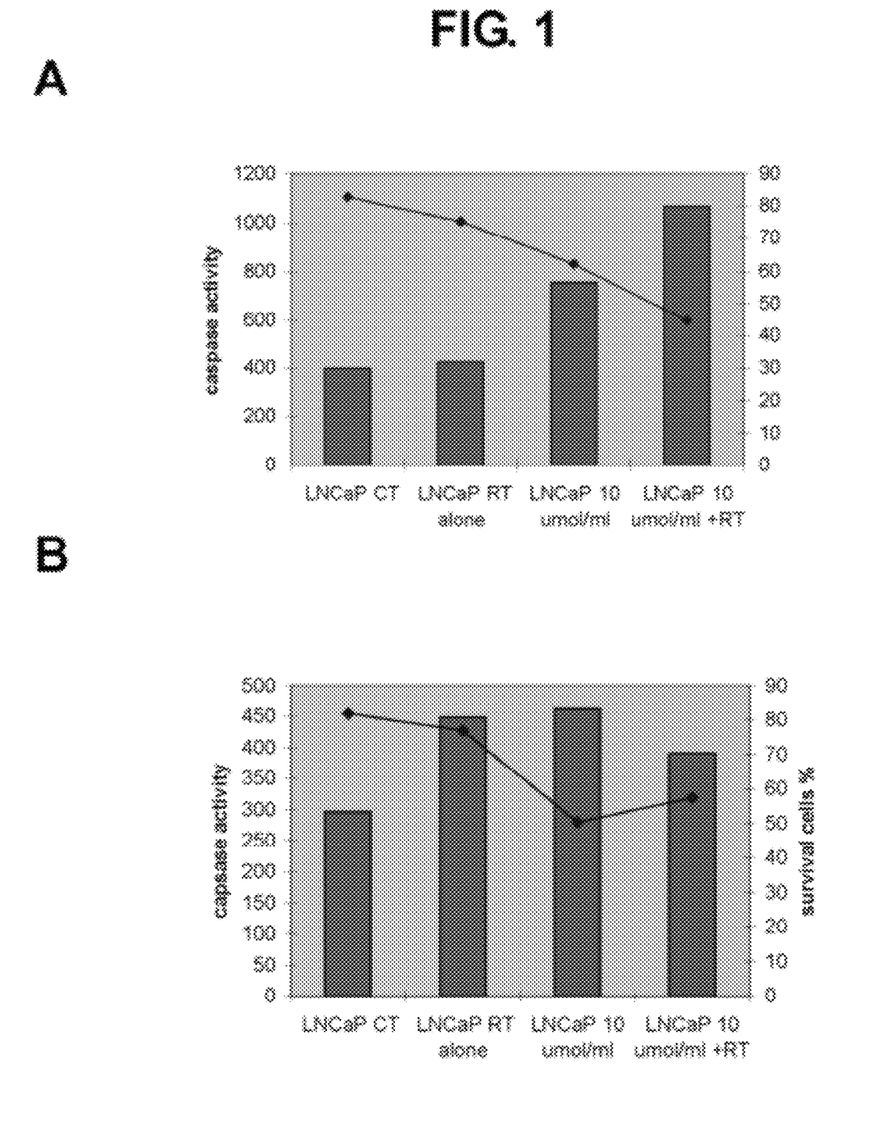
FIG. 1. Depicts the in vitro effects of 1-O-octadecyl-2-O-methyl-glycero-3-phosphocholine (final concentration 10 μM), (ionizing) radiation (absorbed dose of 5 Gray units; indicated as "RT"), and a combination thereof on programmed cell death (apoptosis) and the survival rate of LNCaP androgen-sensitive human prostate adenocarcinoma cells. Apoptosis was determined using the Apo-ONE™ Homogenous Caspase-3/7 Assay, Promega, Inc., Madison, Wis., USA according to the manufacturers instructions. The percentage of living cancer cells was estimated by means of trypan blue dye exclusion as described (Freshney, R. I. (1994) *Culture of Animal Cells: A Manual of Basic Technique*. 3rd Ed. Wiley-Liss. New York. USA). The cells were exposed to radiation six hours after (FIG. 1A), concomitantly with (FIG. 1B), or six hours before administration of 1-O-octadecyl-2-O-methyl-glycero-3-phospho-choline (FIG. 1C). The caspase assay was performed 12 hours after exposure to radiation. The respective data shown represent the average of two independent experiments.

The cells were exposed to radiation six hours after (FIG. 1A), concomitantly with (FIG. 1B), or six hours before administration of 1-O-octadecyl-2-O-methyl-glycero-3-phospho-choline (FIG. 1C). The caspase assay was performed 12 hours after exposure to radiation. The respective data shown represent the average of two independent experiments.

When 1-O-octadecyl-2-O-methyl-glycero-3-phosphocholine was administered six hours prior to exposing the cells to radiation the combined treatment resulted in a survival of only about 45% of the tumor cells as compared to about 85% in untreated controls. Accordingly, in the treated cells a significant increase (>2.5 fold) in apoptotic response was observed (as determined by the caspase-3/7 assay). Individual treatment with radiation or 1-0-octadecyl-2-O-methyl-glycero-3-phosphocholine resulted in intermediate survival rates of about 75% and about 60%, respectively (FIG. 1A).

In case of a concomitant administration of radiation and 1-O-octadecyl-2-O-methyl-glycero-3-phosphocholine to the cells the survival rate was determined to be about 55%, which is in the same range as observed for the individual chemical treatment (about 50%). Exposure of the cells only to radiation resulted in a survival rate of about 80%, which is comparable to the untreated controls (about 86%). Surprisingly, the results of the caspase-3/7 assays were similar for the individual and the combined treatment (FIG. 1B).

When 1-O-octadecyl-2-O-methyl-glycero-3-phosphocholine was administered six hours after exposing the cells to radiation the combined treatment resulted in a survival of about 40% of the cells, which is in the same range as observed for the individual chemical treatment (about 45%). Exposure of the cells only to radiation resulted in a survival rate of about 70%. The extent of apoptosis observed was about 25% increased in the cells only exposed to the chemical as compared to the cells exposed to the combined treatment (FIG. 1C).

Based on the above results it appears as if administration of 1-O-octadecyl-2-O-methyl-glycero-3-phosphocholine prior to exposing the cells to radiation results in the most significant effect on cell survival rates and apoptotic response.

In a further approach, 10 μM 1-O-octadecyl-2-O-methyl-glycero-3-phosphocholine (final concentration; "CHEM") and (ionizing) radiation (5 Gray units; "RT") were administered simultaneously to the LNCaP cells but the subsequent incubation period was extended to 24 hours. Apoptosis was measured using the Apo-ONE™ Homogenous Caspase-3/7 Assay as described above and expressed as relative fluorescence units (RFLU). The percentage of apoptotic cells was determined by flow cytometric analysis of annexin V-PE positive-stained and 7-AAD (7-Amino ActinomycinD) negative-stained cells (both purchased from BD Biosciences, San Jose, Calif., USA) according to established standard protocols. The results are summarized in the following table. The data represent means±SEM from three independent experiments.

| Treatment | % Annexin V-PE pos. cells | Caspase-3/7 activity (RFLU) |
|---|---|---|
| Control | 3.6 ± 0.2 | 193 ± 39 |
| CHEM | 18.6 ± 1.0 | 580 ± 207 |
| RT | 5.0 ± 0.6 | 242 ± 36 |
| CHEM + RT | 31.7 ± 1.0* | 1514 ± 102* |

The statistical significance of the results was calculated using the one-way ANOVA, LSD test.
*$p < 0.0001$ compared to each of the individual treatments CHEM and RT, respectively.

The enhancement of apoptosis in the "CHEM+RT" treated cells was also observed in androgen-insensitive LNCaP $C_{4-2}$ and LNCaP-Res cells (data not shown).

Next, the interaction of 1-O-octadecyl-2-O-methyl-glycero-3-phosphocholine administration ("CHEM") and androgen deprivation ("AD") was investigated. LNCaP cells were deprived of androgen for two days by charcoal absorption of serum according to established procedures well known in the art. CHEM was added in a final concentration of 5 μM and 10 μM, respectively. In addition, it was tested whether addition of the synthetic androgen R1881 ("R1881") two days prior to CHEM administration resulted in reversal of the effect.

Apoptosis was measured using the Apo-ONE™ Homogenous Caspase-3/7 Assay as described above and expressed as relative fluorescence units (RFLU). The percentage of apoptotic cells was determined via annexin V-PE/7-AAD staining as described above. The caspase-317 assay and annexin staining were performed 22 hours after CHEM treatment. The results are summarized in the following table.

| Treatment | % Annexin V-PE pos. cells | Caspase-3/7 activity (RFLU) |
|---|---|---|
| Contr. | 9.6 | 235 |
| Contr. + 5 μM CHEM | 13.0 | 380 |
| Contr. + 10 μM CHEM | 17.5 | 436 |
| AD | 12.6 | 81 |
| AD + 5 μM CHEM | 15.4 | 126 |
| AD + 10 μM CHEM | 27.4 | 115 |
| AD + R1881 | 7.0 | 130 |
| AD + R1881 + 5 μM CHEM | 14.6 | 453 |
| AD + R1881 + 10 μM CHEM | 21.6 | 962 |

As apparent from the above results, administration of 1-O-octadecyl-2-O-methyl-glycero-3-phosphocholine to androgen-deprived LNCaP cells resulted in a dose-dependent significant increase in apoptotic response. Furthermore, this effect was not reversed by adding a synthetic androgen to the medium prior to 1-O-octadecyl-2-O-methyl-glycero-3-phosphocholine treatment.

Additionally, in a preliminary study the in vivo effects of 1-O-octadecyl-2-O-methyl-glycero-3-phosphocholine, (ionizing) radiation, and a combination thereof on LNCaP cells grown orthotopically in the prostates of nude mice (seven mice/group) was investigated.

1-O-octadecyl-2-O-methyl-glycero-3-phosphocholine was administered intraperitoneally in a dose of 30 mg/kg body weight/day administered intraperitoneally for 15 days (FIG. 2A; studies using different routes of administration such as orally or by gavage are currently under way). The (ionizing) radiation corresponds to an absorbed dose of 5 Gray units administered on day 7 (FIG. 2C). The combined treatment is illustrated in FIG. 2B. Tumor growth was assessed via determining the serum level of the prostate-specific antigen (PSA) using a commercially available test kit as well as the tumor volume by means of magnetic resonance imaging.

Figure 2:
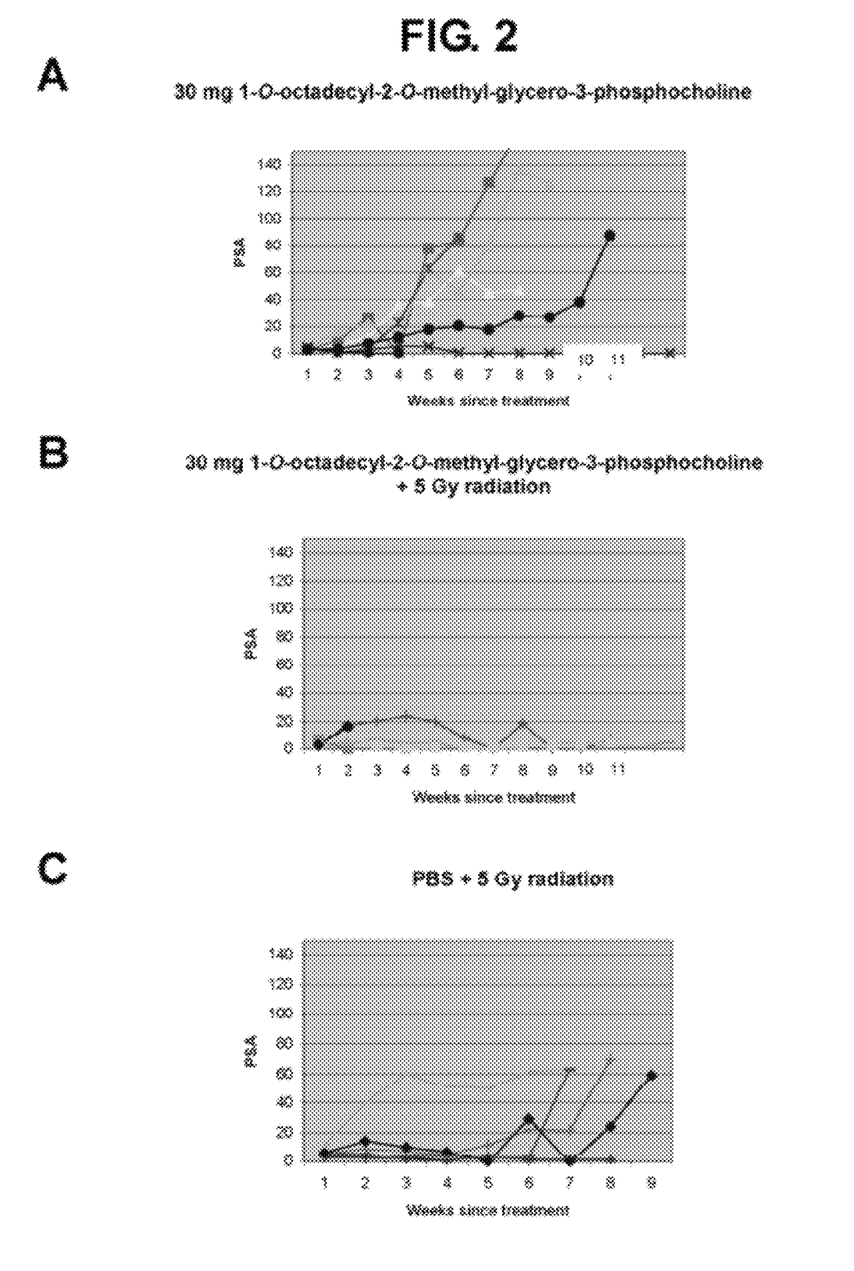

As can be seen, the combined treatment resulted in a significant decrease of PSA serum levels as compared to either individual treatment ("PBS" represents phosphate-buffered saline) demonstrating that the in vitro results can also be transferred to an in vivo setting.

EMBODIMENTS

1. Method for determining whether a small molecule is a functional replacement for a protein or peptide ligand of a cellular receptor and providing that the small molecule is a therapeutically useful agent in the treatment of diseases where the modulation of this receptor will lead to a therapeutic effect, the method comprising measuring the effect of both the receptor ligand and the small molecule on a panel of at least 3 different permanent cell lines and/or primary cells and the biological effects on this cell panel of both compounds are qualitatively similar and correlate to the quantitative presence of the receptor in the respective cell of the panel.

2. The method according to embodiment 1, wherein the biological effects of both the small molecule and the protein or peptide receptor ligand on the cells are measured individually and in combination.

3. The method according to embodiment 1 or 2, wherein the biological effects of both the small molecule and the protein or peptide receptor ligand are measured in the presence of at least one additional compound, wherein the at least one additional compound is selected from the group consisting of a protein, a peptide or a small molecule.

4. The method according to embodiment 3, wherein the similarity of the biological effects of the small molecule and the protein or peptide receptor ligand, as well as their combinations with the additional compound or the panel of additional compounds is similar.

5. The method according to embodiment 4, wherein the similarity of the biological effect of the measured compounds comprises a matrix of biological data of at least three cell lines and at least three compounds, measured either individually and/or in combinations of two and/or combinations of three or more compounds and the similarity between the small molecule and the protein or peptide receptor ligand is computed from this matrix of data by established mathematical methods.

6. The method according to embodiment 5, wherein the similarity of the small molecule and the receptor ligand is calculated from the biological data matrix and being greater than a reasonable threshold, that differentiates random ad hoc combinations from therapeutically useful compounds and/or combinations of compounds.

7. The method according to embodiment 3 for determining if the combination of the small molecule with one of the additional compounds results in a synergistic biological effect.

8. The method according to any of embodiments 1 to 7, wherein said small molecule is a phospholipid, and in particular AP-121.

9. The method according to any of embodiments 1 to 7, wherein said receptor ligand is a protein or peptide, selected from an agonistic FAS antibody or a FAS binding protein and the receptor of interest is the FAS receptor.

10. The method according to embodiment 1, where a small molecule is being identified as an activator of the FAS receptor, comprising measuring the effects of both a FAS receptor protein or peptide ligand and a small molecule on a panel of at least 3 different permanent cell lines and/or primary cells with different levels of FAS receptor expression and the biological effects on this cell panel of both compounds is qualitatively similar and directly correlates to the quantitative presence of the FAS receptor in the respective cell of the panel.

11. The method according to embodiment 10, wherein the biological effects of both the small molecule and the FAS receptor protein or peptide ligand is each measured alone and in combination with at least one additional compound, being either a protein, a peptide or an other small molecule.

12. The method according to embodiment 11, wherein the biological effects of both the small molecule and the FAS receptor ligand is each measured alone in combination with an array of at least two additional compounds, being either proteins, peptides or small molecules.

13. The method according to embodiment 11 or 12, where the small molecule is AP-121 and the additional compound or the array of compounds is selected from one or more anti-tumor agents, wherein the anti-tumor agent is selected from 16-Aza-epothilone B, Aldesleukin, Amifostine, Aranose, Bevacizumab, Bleocin, Bleomycin, BMS-184476, Bortezomib, Calcitriol, Camptothecin, Canertinib, Canfosfamide, Capecitabine, Carboplatin, Carmustine, Cefixime, Ceftriaxone, Celecoxib, Celmoleukin, Cetuximab, Ciclosporin, Cisplatin, Clodronate, Cyclophosphamide, Cytarabine, Dasitinib, Deoxorubicin, Desoxyepothilone B, Diethylstilbestrol, Diflomotecan, Docetaxel, Doxorubicin, Edatrexate, Efaproxiral, EKB-569, Epirubicin, Epratuzumab, Erlotinib, Etoposide, Exatecan, Fludarabine, Fluorouracil, Folinic acid, Galarubicin, Gefinitib, Gemcitabine, Gemtuzumab, Gimatecan, Glufosfamide, Granisetron, Homoharringtonine, Hyaluronic acid, Ibandronate, Ibritumomab, Ifosfamide, Imatinib, Interferon alfa, Interferon alfa-2a, Interferon alfa-2b, Irinotecan, Isoflavone, Isotretinoin, Ixabepilone, Ketoconazole, Lapatinib, Leflunomide, Lenograstim, Leucovorin, Lexidronarn, Linezolid, Lometrexol, Lurtotecan, MEN10755, Melfalan, Methotrexate, Mitomycin, Neridronate, Neuradiab, Nimesulide, Nitroglycerin, 06-Benzylguanine, Omeprazole, Ortataxel, Oxaliplatin, Paclitaxel, Patupilone, Pegfilgrastim, PEG-filgrastim, Pelitinib, Pemetrexed, Pentostatin, Perifosine, Plevitrexed, Polyprenoic acid, Quinupristin, Raloxifene, Raltitrexed, Ramosetron, Retinoic acid, Risedroante, Rituximab, Rofecoxib, Rubitecan, S-9788, Sabarubicin, Sargramostim, Satraplatin, SN-38, Sorafenib, Suberanilohydroxamic acid, Sutent, Tamoxifen, Taxotere, Tazarotene, Tegafur, Temozolamide, Tesmilifene, Tetrodotoxin, Thalidomide, Tipifarnib, Topotecan, Trabectedin, Trastuzumab, Traszutumab, Treosulfan, Tretinoin, Vatalanib, Vincristine, Vinorelbine, Vincristine, ZD-6474, Zoledronate or Zosuquidar.

14. The method according to embodiment 11 or 12, where the small molecule is AP-121 and the additional compound is a compound selected from one or more antiviral agents, wherein the antiviral agent is selected from 3TC, Abacavir, Adefovir dipivoxil, Acyclovir, Amprenavir, Amantadine, Arnoxovir, AZT, Clevudine, Delavirdine, d4T, Emtricitabine, Entecavir, Famciclovir, Ganciclovir, Indinavir, Lamivudine, Nelfinavir, Nevirapine, Oseltamavir, Rimantadine, Ritonavir, Saquinavir, Septrin, Telbivudine, Tenofovir, Valacyclovir, Valtorcitabine, Valopicitabine or Zanamivir.

15. The method according to embodiment 13 or 14, comprising measuring the combination of AP-121 with one of the additional compounds and determining if a synergistic biological effect is affected by said combination on the panel of cells.

16. The use of a combination of compounds as defined in embodiment 15, for the manufacture of a medicament for the treatment of a medical condition selected from the group consisting of cancer and viral diseases.

17. The use of embodiment 16, wherein the combination of compounds comprises AP-121 and another compound selected frOm the group consisting of temozolamide, cisplatin, carboplatin, satraplatin, gemcitabine, doxorubicine, or camptothecin.

18. Method for the identification a therapeutically useful diagnostic biomarker for establishing the utility of AP-121 as a therapeutically useful functional replacement of the FAS receptor ligand, comprising the measurement of the activity status of the FAS receptor in human cells that are taken from human patients and the ability of AP-121 to activate the FAS receptor in said human cells.

19. The method according to embodiment 18, further comprising selecting a therapeutic indication for AP-121, based on the functional activity status of the FAS receptor and its correlation to a particular disease.

20. AP-121 for use as a therapeutically useful agent to treat diseases where normal FAS receptor signaling through the endogenous FAS ligand is impaired, but the FAS receptor is still being expressed and present in cells that mediate a particular disease, wherein the disease is selected from the group consisting of glioblastoma multiforme, non-small lung cancer, and esophageal cancer.

21. AP-121 for use as a therapeutically useful agent to treat diseases where normal FAS receptor signaling through the endogenous FAS ligand is impaired, but the FAS receptor is still being expressed and present in cells that mediate a particular disease, wherein the disease is selected from the group consisting of glioblastoma multiforme, non-small lung cancer, and esophageal cancer.

22. The method according to embodiment 18 or 19, wherein the FAS receptor expression in patients cells is determined via RT-PCR.

23. The method according to embodiment 18 or 19, wherein the FAS receptor presence in the membrane of human cells is determined via a binding anti-body or an other FAS receptor binding protein or a labeled peptide that binds to the FAS receptor.

24. A combination of compounds, comprising AP-121 in combination with a FAS receptor agonistic anti-body, that is synergistic with AP-121 in activating the FAS receptor.

25. A pharmaceutical formulation comprising a small molecule according to embodiment 1.

26. The pharmaceutical formulation according to embodiment 25, wherein the formulation is a dosage form for, oral application 27. The pharmaceutical formulation according to embodiment 25 or 26, wherein the formulation is a solid dosage form.

28. The pharmaceutical formulation according to any of embodiments 25 to 27, comprising AP-121, or an enantiomer or diastereomer or a pharmaceutically acceptable salt thereof and at least one pharmaceutically acceptable excipient.

29. The pharmaceutical solid dosage form according to embodiment 28, wherein AP-121 is present in crystalline form.

30. The pharmaceutical solid dosage form according to any of embodiments 28 or 29, wherein the amount of AP-121 is in the range of 30 to 250 mg.

31. The pharmaceutical solid dosage form according to embodiment 30, wherein the amount of AP-121 is in the range of 50 to 150 mg.

32. The pharmaceutical solid dosage form according to any of embodiments 25 to 31, wherein the dosage form is selected from the group consisting of tablets, pills, capsules, and granules.

33. The pharmaceutical solid dosage form according to any of embodiments 25 to 32, wherein the dosage form is an enteric dosage form.

34. Method for the treatment of cancer, comprising administering to a patient a pharmaceutical formulation according to any of embodiments 25 to 33 in combination with radiation therapy to enhance the therapeutic benefit of the radiation treatment.

35. The method according to embodiment 34, wherein the cancer is selected from the group consisting of prostate cancer, non-small cell lung cancer, brain cancer, and head and neck cancer.

36. The method according to embodiment 34 or 35, wherein the pharmaceutical formulation is administered before, during and/or after a radiotherapy treatment of cancer.

The present invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modifications and variations of the inventions embodied therein herein disclosed may be resorted to by those skilled in the art, and that such modifications and variations are considered to be within the scope of this invention.

All documents cited or referenced herein including any manufacturer's instructions, descriptions, product specifications, and product sheets for any products mentioned herein or in any document referenced herein are hereby incorporated by reference, and may be employed in the practice of the invention. Citation or identification of any document in this application is not an admission that such document is available as prior art to the present invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:
1. A method for the treatment of cancer, comprising:
administering to a subject in need thereof a synergistically effective amount of AP-121 and at least one anti-tumor agent, wherein the anti-tumor agent is temozolamide or gemcitabine.

* * * * *